United States Patent
Han et al.

(10) Patent No.: US 9,955,935 B2
(45) Date of Patent: May 1, 2018

(54) RADIOGRAPHY APPARATUS AND METHOD FOR CONTROLLING THE RADIOGRAPHY APPARATUS

(71) Applicant: SAMSUNG ELECTRONICS CO., LTD., Suwon-si (KR)

(72) Inventors: Seok Min Han, Seongnam-si (KR); Dong-Goo Kang, Hwaseong-si (KR); Young Hun Sung, Hwaseong-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 193 days.

(21) Appl. No.: 14/838,636

(22) Filed: Aug. 28, 2015

(65) Prior Publication Data

US 2016/0206271 A1    Jul. 21, 2016

(30) Foreign Application Priority Data

Jan. 20, 2015    (KR) .................... 10-2015-0009376

(51) Int. Cl.
*G06K 9/00*    (2006.01)
*A61B 6/00*    (2006.01)
(Continued)

(52) U.S. Cl.
CPC ............ *A61B 6/5264* (2013.01); *A61B 6/481* (2013.01); *A61B 6/504* (2013.01); *A61B 6/5217* (2013.01); *A61B 6/5235* (2013.01); *G06K 9/6204* (2013.01); *G06T 5/50* (2013.01); *A61B 6/4035* (2013.01); *G06T 2207/10016* (2013.01); *G06T 2207/10116* (2013.01);
(Continued)

(58) Field of Classification Search
CPC ....... A61B 6/5264; A61B 6/481; A61B 6/504; A61B 6/5217; A61B 6/5235; A61B 6/4035; G06K 9/6204; G06T 5/50; G06T 2207/10016; G06T 2207/10116; G06T 2207/20064; G06T 2207/20224; G06T 2207/30101; G06T 2207/30104
See application file for complete search history.

(56) References Cited

U.S. PATENT DOCUMENTS 6,373,920 B1 * 4/2002 Hsieh ................... A61B 6/481
                                                                378/8
8,285,014 B2 * 10/2012 Lauritsch ............ A61B 6/4441
                                                                378/4
(Continued)

FOREIGN PATENT DOCUMENTS

JP    2005-199041 A    7/2005

*Primary Examiner* — Shefali Goradia
(74) *Attorney, Agent, or Firm* — Sughrue Mion, PLLC

(57) ABSTRACT

A radiography apparatus and a method for controlling the radiography apparatus are provided. The radiography apparatus includes a radiographer configured to acquire a first radiation image of a subject before a contrast reagent is injected into the subject, and acquire a second radiation image of the subject after the contrast reagent is injected into the subject. The radiography apparatus further includes an image processor configured to calculate a difference between data of a pixel of the first radiation image and data of a pixel of the second radiation image, for each of pixels of the first radiation image, and acquire an image of the subject based the difference for each of the pixels of the first radiation image.

21 Claims, 26 Drawing Sheets

(51) Int. Cl.
*G06K 9/62* (2006.01)
*G06T 5/50* (2006.01)

(52) U.S. Cl.
CPC ............ *G06T 2207/20064* (2013.01); *G06T 2207/20224* (2013.01); *G06T 2207/30101* (2013.01); *G06T 2207/30104* (2013.01)

(56) References Cited

U.S. PATENT DOCUMENTS

| | | | | |
|---|---|---|---|---|
| 9,025,840 B2 * | 5/2015 | Waechter-Stehle | ... | G06T 7/2053 378/98.12 |
| 2007/0104317 A1 * | 5/2007 | Ohishi | ... | A61B 6/504 378/98.12 |

* cited by examiner

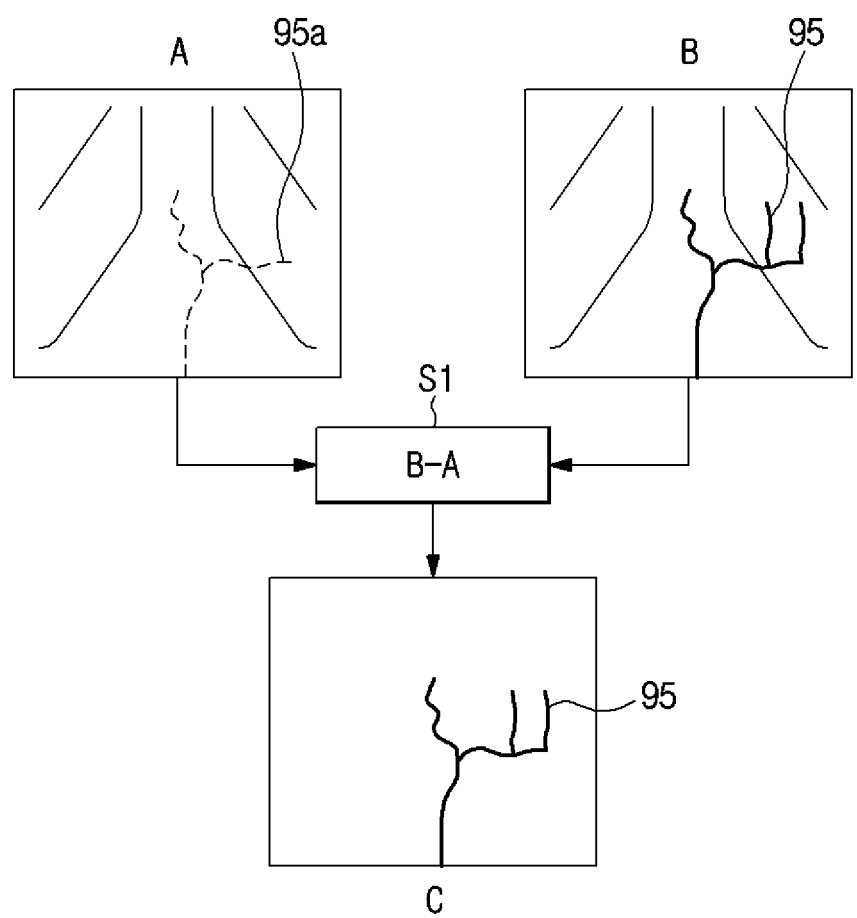

FIG.10

| FIRST RADIATION IMAGE A | | SECOND RADIATION IMAGE B | DIFFERENCE (ABSOLUTE VALUE) |
|---|---|---|---|
| PIXEL | DATA | DATA | |
| A11 | 100 | 100 | 0 |
| A12 | 101 | 100 | 1 |
| ⋮ | ⋮ | ⋮ | ⋮ |
| A55 | 98 | 100 | 2 |

FIG.12

| FIRST RADIATION IMAGE A | | SECOND RADIATION IMAGE B | DIFFERENCE (ABSOLUTE VALUE) |
|---|---|---|---|
| PIXEL | DATA | DATA | |
| A11 | 100 | 200 | 100 |
| A12 | 101 | 200 | 99 |
| ⋮ | ⋮ | ⋮ | ⋮ |
| A55 | 98 | 200 | 102 |

RADIOGRAPHY APPARATUS AND METHOD FOR CONTROLLING THE RADIOGRAPHY APPARATUS

CROSS-REFERENCE TO RELATED APPLICATION

This application claims priority from Korean Patent Application No. 10-2015-0009376, filed on Jan. 20, 2015, in the Korean Intellectual Property Office, the disclosure of which is incorporated herein by reference in its entirety.

BACKGROUND

1. Field

Apparatuses and methods consistent with exemplary embodiments relate to a radiography apparatus and a method for controlling the radiography apparatus.

2. Description of the Related Art

A radiography apparatus irradiates radiation such as X-rays to a subject, and receives radiation transmitted through the subject to acquire images about an inside of the subject. The radiography apparatus can acquire information about the inside of the subject using such a property of radiation that is absorbed or transmitted according to properties of a material it passes through.

The radiography apparatus is used in various fields. For example, the radiography apparatus is used to detect lesions in a human body, and to understand inside structures of objects and elements. Also, the radiography apparatus is used to scan baggage in an airport or harbor. Examples of the radiography apparatus include Digital Radiography (DR), Computed Tomography (CT), Full Field Digital Mammography (FFDM), an angiography apparatus, and Positron Emission Tomography (PET).

SUMMARY

Exemplary embodiments address at least the above problems and/or disadvantages and other disadvantages not described above. Also, the exemplary embodiments are not required to overcome the disadvantages described above, and may not overcome any of the problems described above.

Exemplary embodiments provide a radiography apparatus that is capable of reducing or removing an artifact on an image, which may be generated by radiography, and a method of controlling the radiography apparatus.

According to an aspect of an exemplary embodiment, there is provided a method of controlling a radiography apparatus, the method including acquiring a first radiation image of a subject before a contrast reagent is injected into the subject, and acquiring a second radiation image of the subject after the contrast reagent is injected into the subject. The method further includes calculating a difference between data of a pixel of the first radiation image and data of a pixel of the second radiation image, for each of pixels of the first radiation image, and acquiring an image of the subject based on the difference for each of pixels of the first radiation image.

The calculating may include calculating a difference between data of a pixel in an area of the first radiation image and data of a pixel in an area of the second radiation image, for each of pixels in the area of the first radiation image.

The data of the pixel of the first radiation image and the data of the pixel of the second radiation image may include at least one among pixel intensities, values acquired by edge detection, and wavelet coefficients.

The method may further include dividing the first radiation image into first areas, and dividing the second radiation image into second areas.

At least two of the first areas of the first radiation image may have an overlapping part, or at least two of the second areas of the second radiation image may have an overlapping part.

At least one of the first areas of the first radiation image may have a size that is different from a size of one or more remaining ones of the first areas, or at least one of the second areas of the second radiation image may have a size that is different from a size of one or more remaining ones of the second areas.

The method may further include subtracting the first radiation image from the second radiation image to acquire a difference image. The acquiring may include correcting the difference image based on the difference for each of the pixels of the first radiation image, to acquire the image.

The method may further include determining a degree of difference based on the difference for each of the pixels of the first radiation image, for each of pixels of the second radiation image. The acquiring may include acquiring the image based on the degree of difference for each of the pixels of the second radiation image.

The first radiation image may be of a high resolution, and the second radiation image may be of the high resolution. The calculating may include down-sampling the first radiation image of the high resolution and the second radiation image of the high resolution to acquire the first radiation image of a low resolution and the second radiation image of the low resolution, and calculating a difference between data of a pixel of the first radiation image of the low resolution and data of a pixel of the second radiation image of the low resolution, for each of pixels of the first radiation image of the low resolution.

The method may further include determining a degree of difference based on the difference for each of the pixels of the first radiation image of the low resolution, for each of pixels of the second radiation image of the low resolution, and acquiring an image of the low resolution based on the degree of difference for each of the pixels of the second radiation image of the low resolution. The acquiring the image of the subject may include up-sampling the image of the low resolution to acquire the image of the subject.

According to an aspect of an exemplary embodiment, there is provided a radiography apparatus including a radiographer configured to acquire a first radiation image of a subject before a contrast reagent is injected into the subject, and acquire a second radiation image of the subject after the contrast reagent is injected into the subject. The radiography apparatus further includes an image processor configured to calculate a difference between data of a pixel of the first radiation image and data of a pixel of the second radiation image, for each of pixels of the first radiation image, and acquire an image of the subject based the difference for each of the pixels of the first radiation image.

The image processor may be configured to calculate a difference between data of a pixel in an area of the first radiation image and data of a pixel in an area of the second radiation image, for each of pixels in the area of the first radiation image.

The image processor may be further configured to divide the first radiation image into first divided areas, and divide the second radiation image into second divided areas.

The image processor may be further configured to subtract the first radiation image from the second radiation image to acquire a difference image, and correct the difference image based on the difference for each of the pixels of the first radiation image, to acquire the image.

The image processor may be further configured to determine a degree of difference based on the difference for each of the pixels of the first radiation image, for each of pixels of the second radiation image, and acquire the image based on the degree of difference for each of the pixels of the second radiation image.

The first radiation image may be of a high resolution, and the second radiation image may be of a high resolution. The image processor may be further configured to down-sample the first radiation image of the high resolution and the second radiation image of the high resolution to acquire the first radiation image of the low resolution and the second radiation image of the low resolution, and calculate a difference between data of a pixel of the first radiation image of the low resolution and data of a pixel of the second radiation image of the low resolution, for each of pixels of the first radiation image of the low resolution.

The image processor may be further configured to determine a degree of difference based on the difference for each of the pixels of the first radiation image of the low resolution, for each of pixels of the second radiation image of the low resolution, acquire an image of the low resolution based on the degree of difference for each of the pixels of the second radiation image of the low resolution, and up-sample the image of the low resolution to acquire the image of the subject.

According to an aspect of an exemplary embodiment, there is provided a radiography apparatus including an image processor configured to calculate a difference between data of a pixel of a first radiation image of a subject without a contrast reagent and data of a pixel of a second radiation image of the subject with the contrast reagent, for each of pixels of the first radiation image. The image processor is further configured to determine a degree of difference based on the difference for each of the pixels of the first radiation image, for each of pixels of the second radiation image, and acquire an image of the subject based on the degree of difference for each of the pixels of the second radiation image.

The image processor may be further configured to subtract the first radiation image from the second radiation image to acquire a difference image, and apply, to the difference image, the degree of difference for each of the pixels of the second radiation image, to acquire the image.

The degree of difference may be a smallest or greatest value among the difference for each of the pixels of the first radiation image, or an average value of the difference for each of the pixels of the first radiation image.

BRIEF DESCRIPTION OF THE DRAWINGS

The above and/or other aspects will be more apparent by describing certain exemplary embodiments with reference to the accompanying drawings in which:

FIG. 8A is a diagram of a process of acquiring a difference image according to an exemplary embodiment;

FIG. 10 is a table used in the method of FIG. 10;

FIG. 12 is a table used in the method of FIG. 11;

DETAILED DESCRIPTION OF THE EXEMPLARY EMBODIMENTS

Figure 1:
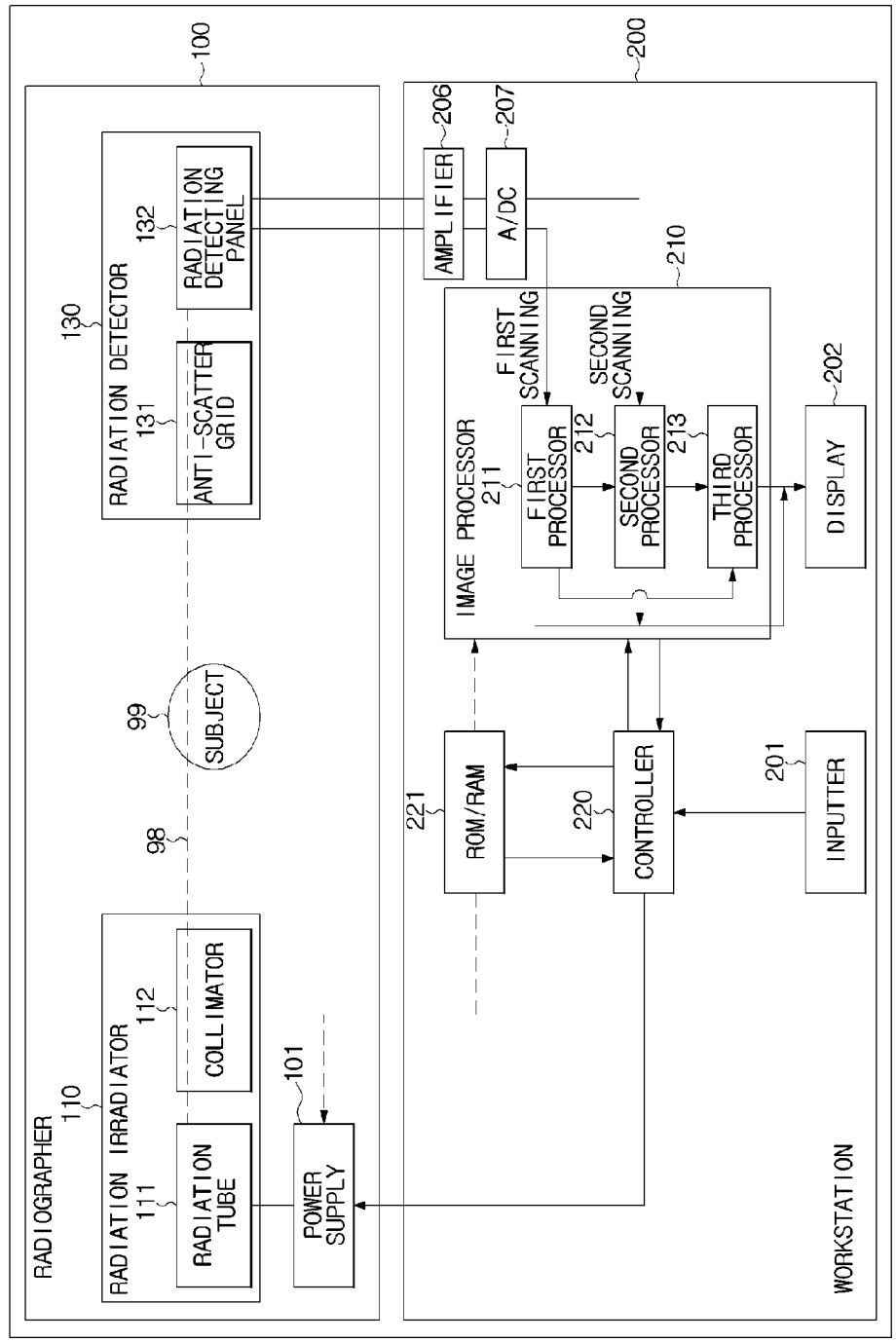
FIG. 1 is a block diagram of a radiography apparatus according to an exemplary embodiment.

Exemplary embodiments are described in greater detail herein with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

It will be understood that the terms "comprises" and/or "comprising" used herein specify the presence of stated features or components, but do not preclude the presence or addition of one or more other features or components. In addition, the terms such as "unit", "-er (-or)", and "module" described in the specification refer to an element for performing at least one function or operation, and may be implemented in hardware, software, or the combination of hardware and software.

Figure 2:
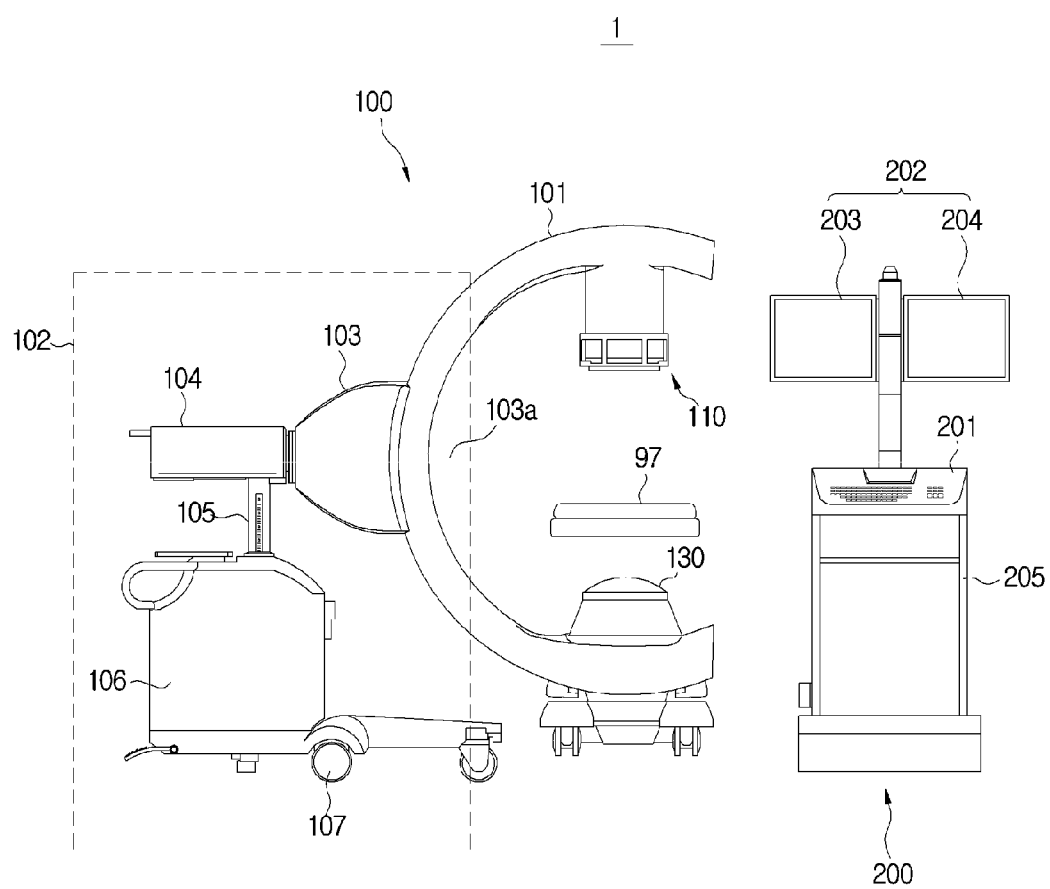
FIG. 2 is a view of the radiography apparatus of FIG. 1.

FIG. 1 is a block diagram of a radiography apparatus 1 according to an exemplary embodiment, and FIG. 2 is a view of the radiography apparatus 1 of FIG. 1.

As shown in FIGS. 1 and 2, the radiography apparatus 1 includes a radiographer 100 and a workstation 200 communicatively connected to the radiographer 100.

The radiographer 100 may be communicatively connected to the workstation 200 through a cable or a wireless communication network. Various data acquired by the radiographer 100 may be transferred in the form of electrical signals to the workstation 200, and various control signals generated by the workstation 200 may be also transferred in the form of electrical signals to the radiographer 100.

The radiographer 100 uses radiation 98 to acquire data about an inside of a subject 99. In order to use the radiation 98 to acquire data about the inside of the subject 99, the radiographer 100 includes a radiation irradiator 110 configured to irradiate the radiation 98 to the subject 99, and a radiation detector 130 configured to receive radiation transmitted through the subject 99, and output electrical signals according to the received radiation.

The radiation irradiator 110 generates the radiation 98 of a predetermined energy spectrum, and irradiates the generated radiation 98 toward the subject 99. The radiation irradiator 110 includes a radiation tube 111 configured to generate radiation 98, and irradiate the generated radiation 98 toward the subject 99, and a collimator 112 configured to filter the radiation irradiated from the radiation tube 111. The radiation tube 111 is electrically connected to a power supply 101, and receives a supply voltage needed for generating the radiation 98 from the power supply 101.

The radiation 98 emitted by the radiation irradiator 110 is irradiated to the subject 99, and then transmitted through the subject 99. Herein, the subject 99 may be a living thing, such as a human body or animal, or a non-living thing, such as a baggage, a machine tool, or a building.

The radiation 98 irradiated to the subject 99 may be absorbed in a material inside the subject 99, or may attenuate at a rate to be transmitted through the subject 99. In this case, the radiation 98 may attenuate according to an attenuation coefficient of the material inside the subject 99. Different kinds of materials may have different attenuation coefficients. For example, bones of a human body may have a relatively greater attenuation coefficient than other tissues so that they absorb a major part of radiation, and blood vessels of a human body may have a relatively low attenuation coefficient so that they can transmit a major part of radiation. The attenuation coefficient may be decided depending on a property (for example, density) of the material inside the subject 99 at which the radiation 98 arrives.

In detail, an intensity I of radiation transmitted through an internal tissue in the subject 99 may be calculated according to Equation (1) below.

$$I=I_0 e^{-\mu t},\qquad(1)$$

where $I_0$ represents an intensity of radiation irradiated by the radiographer 100, $\mu$ represents an attenuation coefficient according to the internal tissue, etc. of the subject 99, and t represents a thickness of the internal tissue of the subject 99 through which radiation is transmitted. The attenuation coefficient may depend on a kind or structure of the material existing in the subject 99.

The radiation detector 130 receives the radiation 98 transmitted through the subject 99, and outputs electrical signals (hereinafter, referred to as radiation signals) corresponding to the received radiation 98.

The radiation detector 130 includes a radiation detecting panel 132 configured to receive the radiation 98 transmitted through the subject 99, and output the electrical signals corresponding to the received radiation 98, and an anti-scatter grid 131 configured to absorb radiation scattered when it passes through the subject 99 to cause only radiation traveling in a proper direction to arrive at the radiation detecting panel 132. According to another exemplary embodiment, the radiation detector 130 may include, instead of the radiation detecting panel 132, an image intensifier (150 of FIG. 5).

Details about the radiation irradiator 110 and the radiation detector 130 will be described later.

As shown in FIG. 2, the radiographer 100 further includes an installation frame 101 in which the radiation irradiator 110 and the radiation detector 130 are installed, and a driver 102 configured to operate the installation frame 101 according to an irradiation direction or location of radiation, to support operations of the radiation irradiator 110 and the radiation detector 130.

The installation frame 101 has a "C"-shaped structure. The radiation irradiator 110 and the radiation detector 130 are installed at both ends of the "C"-shaped structure such that the radiation irradiator 110 faces the radiation detector 130.

The driver 102 includes a connector 103, a rotation driver 104, an up-down driver 105, a main body 106, and a mover 107. The frame 101 rotates at various angles or move to various positions by the above-mentioned components. Accordingly, the radiation irradiator 110 irradiates the radiation 98 to the subject 99 placed on a table 97, at various positions and in various directions.

The connector 103 connects the installation frame 101 to the rotation driver 104, and may include various components to control the radiation irradiator 110 and the radiation detector 130, or to support control operations of the radiation irradiator 110 and the radiation detector 130.

The rotation driver 104 may include a rotation motor configured to rotate the connector 103 with respect to a predetermined axis 103a, and the installation frame 101 connected to the connector 103, according to a control signal. Accordingly, the radiation irradiator 110 irradiates the radiation 98 to the subject 99 in various directions, and the radiation detector 130 receives radiation in various directions.

The up-down driver 105 may include a bar and a driver configured to move the bar in a direction toward the ground or in a direction counter to the ground. The driver may be installed in the main body 106. The driver may include a motor, and a wheel module configured to rotate according to driving of the motor. The wheel module may be connected to the bar through a toothed wheel, etc. to rotate to move the bar in the direction toward the ground or in the direction counter to the ground.

The main body 106 may include various components for controlling and driving operations of the radiographer 100, such as the driver to move the bar in the direction toward the ground or in the direction counter to the ground. For example, the main body 106 may include the power supply 101 configured to supply a supply voltage that is applied to the radiation irradiator 110. Also, the main body 106 may include a semiconductor chip and a printed circuit board (PCB) configured to perform operations of the radiographer 100. The main body 106 is physically separated by a separate housing, as shown in FIG. 2. However, the main body 106 may be implemented on a ceiling, a floor, and/or a wall of a radiation room.

The main body 106 includes the mover 107 configured to move the main body 106, and the mover 107 may be implemented using a wheel, a rail, or the like.

The workstation 200 controls operations of the radiographer 100, and creates radiation images being visual information that a user can see, based on electrical signals received from the radiographer 100.

The workstation 200 may be a desktop computer, a laptop computer, or a computing apparatus configured to control operations of the radiographer 100, and perform various image processing. The workstation 200 may be an apparatus physically separated from the radiographer 100, as shown in FIG. 2, or may be an apparatus physically coupled with the radiographer 100. The workstation 200 may be implemented with various structures that can be considered by a system designer for controlling radiography or image processing.

As shown in FIG. 1, the workstation 200 includes an amplifier 206, an analog-to-digital converter 207, an image processor 210, a controller 220, and a memory device 221, such as Read Only Memory (ROM) or Random Access Memory (RAM). The image processor 210, the controller 220, and the memory device 221 may be installed in a housing constituting a main body 205 of FIG. 2 of the workstation 200.

The amplifier 206 amplifies electrical signals output from the radiation detector 130. According to another exemplary embodiment, the amplifier 206 may be installed in the radiographer 100. Also, the amplifier 206 may be omitted.

The analog-to-digital converter 207 converts an electrical signal in an analog format into a digital signal in a digital format. In detail, the analog-to-digital converter 207 may convert an analog signal into a digital signal according to a predetermined sampling rate. However, the analog-to-digital converter 207 may be omitted.

The image processor 210 creates a radiation image using the electrical signals received from the radiation detector 130, and may perform various image processing related to the radiation image.

The image processor 210 includes a first processor 211, a second processor 212, and a third processor 213. The first processor 211, the second processor 212, and the third processor 213 may be physically or logically separated from each other. If the first processor 211, the second processor 212, and the third processor 213 are physically separated from each other, the first processor 211, the second processor 212, and the third processor 213 may be implemented as a plurality of semiconductor chips, and if the first processor 211, the second processor 212, and the third processor 213 are logically separated from each other, the first processor 211, the second processor 212, and the third processor 213 may be implemented as a single semiconductor chip.

The first processor 211 creates a radiation image based on the received electrical signals. Also, the first processor 211 may apply one or more lookup tables LUT to the created radiation image, or may apply various filters, such as a low-pass filter or a high-pass filter, to the created radiation image, to further perform image processing on the created radiation image.

The second processor 212 acquires a difference image between a plurality of radiation images (for example, a first radiation image and a second radiation image) created by the first processor 211. The difference image means an image that displays differences between the first radiation image and the second radiation image.

In detail, the second processor 212 may select a pixel of the first radiation image, select a pixel of the second radiation image corresponding to the selected pixel of the first radiation image, and then mathematically subtract a pixel value of the selected pixel of the second radiation image from a pixel value of the selected pixel of the first radiation image, thereby acquiring the difference image. Herein, a pixel means a minimum unit to form an image, and a number of pixels included in an image may decide a resolution of the image.

A pixel value may include a pixel intensity. The pixel intensity represents a degree of brightness of light that is represented by the corresponding pixel, and degrees of brightness of light may be classified into several levels according to predetermined criteria. For example, a pixel intensity of an arbitrary pixel may be set to a value between 0 and 256. In this case, the pixel intensity of 0 may be set to the darkest brightness, and the pixel intensity of 256 may be set to the brightest brightness.

The second processor 212 may add a predetermined weight to at least one among the first radiation image and the second radiation image, and then acquire the difference image between the first radiation image and the second radiation image.

The third processor 213 compares all pixels of the first radiation image to an arbitrary pixel of the second radiation image using the acquired radiation images. The third processor 213 may correct the difference image acquired by the second processor 212 according to results of the comparison, or create a radiation image corresponding to the results of the comparison.

In detail, the third processor 213 may calculate differences between data related to the pixels of the first radiation image and data related to the pixels of the second radiation image, and correct the difference image acquired by the second processor 212 using results of the calculation, or create a radiation image corresponding to the results of the calculation. Herein, the data related to the pixels of the first radiation image or the data related to the pixels of the second radiation image may be at least one among pixel intensities, values acquired by edge detection, values acquired by wavelet transform, and wavelet coefficients.

The values acquired by edge detection mean values acquired by detecting an edge of an image, wherein the edge of the image means an area having a sharp change in brightness in the image. The third processor 213 may detect only an edge(s) from the second radiation image, and then compare pixel values of pixels corresponding to the detected edge(s) to pixel values of all pixels of the first radiation image to thereby acquire resultant data about differences between the pixel values of the first radiation image and the second radiation image.

The wavelet transform means transformation based on a wavelet function. The wavelet transform may be expressed using a basis function of a finite length. A wavelet may be given as vibrations that repeatedly increase or decrease with respect to zero, and the wavelet function means a mathematical expression of such vibrations. The wavelet coefficient means a coefficient that is added to at least one basis function of the wavelet transform. An arbitrary signal can be expressed as a combination of a wavelet coefficient and a basis function. The third processor 213 may calculate differences between data of all pixels of the first radiation image and data of an arbitrary pixel of the second radiation image, using values acquired by the wavelet transform or wavelet coefficients for individual pixels.

The resultant values of edge detection, the resultant values of the wavelet transform, or the wavelet coefficients may be acquired by various methods that can be considered by one of ordinary skill in the art, and because the methods have been well-known in the art, detailed descriptions thereof will be omitted.

Details about operations of the second processor 212 and the third processor 213 will be described later.

The controller 220 controls overall operations of the radiographer 100 and the workstation 200. For example, the controller 220 applies a control signal to the power supply 101 according to electrical signals received from an inputter 201 to enable the power supply 101 to apply a tube voltage and a tube current to the radiation tube 111 of the radiation irradiator 110. Accordingly, the radiation irradiator 110 irradiates the radiation 98 to the subject 99. Also, the controller 220 transfers control signals for controlling operations of the image processor 210.

The memory device 221 may temporarily or non-temporarily store signals output from the controller 220 or information that is to be input to the controller 220, to thereby support operations of the controller 220. Radiation images output from the image processor 210 may also be temporarily or non-temporarily stored in the memory device 221.

The image processor 210 and the controller 220 may be implemented as a Central Processing Unit (CPU) or a Graphic Processing Unit (GPU), wherein the CPU or the GPU may be implemented with one or more semiconductor chips and related components. Also, the memory device 221 may also be implemented with one or more memory semiconductors, a PCB, and related components.

As shown in FIGS. 1 and 2, the workstation 200 includes the inputter 201 and a display 202. The inputter 201 and the display 202 may be connected to the main body 205 through a cable or a wireless communication network.

The inputter 201 receives various information related to operations of the radiography apparatus 1 from a user. The inputter 201 may output an electrical signal according to a user's manipulation, and transfer the electrical signal to the controller 220 to control operations of the radiography apparatus 1. The inputter 201 may be, for example, a keyboard, a mouse, a keypad, a trackball, a track pad, one or more physical buttons, a knob, an operation stick, a touch pad, or a touch screen.

The display 202 may display acquired radiation images or a GPU related information for control of radiography. For example, the display 202 may display, along with the radiation images, information related to operations or settings of the radiography apparatus 1, three-dimensional (3D) images, information about the subject 99, or other various information.

As shown in FIG. 2, according to an exemplary embodiment, the display 202 includes a plurality of displays 203 and 204, and the displays 203 and 204 may display the same image or different images. For example, the display 203 may display an image acquired by the first processor 211, and the display 204 may display an image acquired by the second processor 212 or the third processor 213.

The display 202 may be implemented with a Plasma Display Panel (PDP), Light Emitting Diodes (LEDs), a Liquid Crystal Display (LCD), or a Cathode Ray Tube (CRT). However, the display 202 may be implemented with any other device that can be used to display images.

Hereinafter, the radiation irradiator 110 and the radiation detector 130 of the radiographer 100 will be described in more detail.

Figure 3:
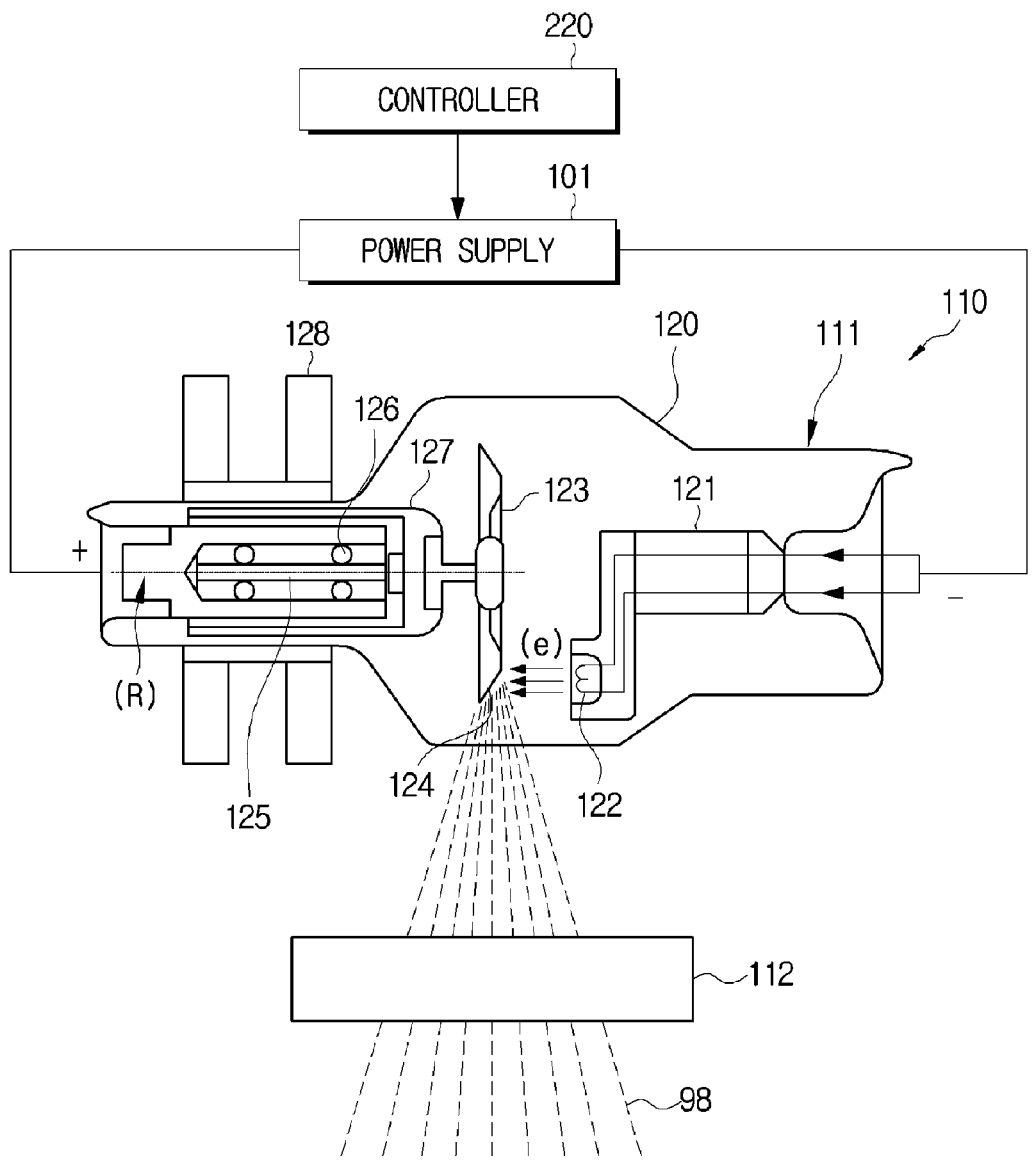
FIG. 3 is a view of a radiation irradiator of FIGS. 1 and 2.

FIG. 3 is a view of the radiation irradiator 110 of FIGS. 1 and 2.

Referring to FIG. 3, the radiation irradiator 110 includes the radiation tube 111 electrically connected to the power supply 101, and the collimator 112 through which the radiation 98 passes.

The power supply 101 applies predetermined voltage and current to the radiation tube 111 under the control of the controller 220 installed in the workstation 200 or the radiographer 100. The power supply 101 may be a commercial power source, or an emergency power source that can be implemented as a separate, independent generator. Also, the power supply 101 may be a storage battery provided in the radiographer 100.

When the predetermined voltage and current is applied from the power supply 101 to the radiation tube 111, the radiation tube 111 generates radiation of a predetermined magnitude according to the predetermined voltage or current. The radiation tube 111 includes a tube body 120, a cathode 121, and an anode 123.

The tube body 120 accommodates various components, such as the cathode 121 and the anode 123, needed to generate radiation, and fixes the components stably to prevent electrons e from leaking out. The tube body 120 may be a glass tube made of silica (hard) glass. An inside of the tube body 120 may be evacuated to a high vacuum state of about $10^{-7}$ mmHg Electronic beams e are irradiated from the cathode 121 toward the anode 123. A filament 122 on which electrons are concentrated is provided at one end of the cathode 121. The filament 122 may be heated according to an applied tube voltage to emit the concentrated electrons e to the inside of the tube body 120, and the emitted electrons e may be accelerated in the tube body 120 to move toward the anode 123. The filament 122 of the cathode 121 may be fabricated with a metal such as tungsten W. According to another exemplary embodiment, a carbon nano tube instead of the filament 122 may be provided at the cathode 121.

The anode 123 generates the radiation 98. When the electrons e emitted and moved from the filament 122 collide with a target surface 124 of the anode 123, the electrons e may decelerate sharply, and the radiation 98 of energy corresponding to the tube voltage may be generated from the target surface 124 according to the deceleration of the electrons e. The target surface 124 is cut in a direction, as shown in FIG. 3, so that the radiation 98 is emitted in a predetermined direction. The anode 123 may be fabricated with a metal such as copper Cu, and the target surface 124 may be formed with a metal, such as tungsten W, chrome Cr, iron Fe, or nickel Ni.

The anode 123 includes a rotary anode that is in a shape of disk. The edge of the rotary anode 123 is cut at a predetermined angle, and accordingly, the target surface 124 is formed on the cut edge. The rotary anode 123 may rotate at predetermined speed with respect to a predetermined rotation axis R. In order to rotate the rotary anode 123, the radiation tube 111 includes a stator 128 configured to form a rotating field, a rotor 127 configured to rotate according to the rotating field formed by the stator 128 to rotate the rotating anode 123, a plurality of bearings 126 configured to rotate according to the rotation of the rotor 127, and a shaft member 125 functioning as the rotation axis R. The rotor 127 may be a permanent magnet.

According to another exemplary embodiment, the anode 123 may be a fixed anode that is in a shape of a cylinder having a cutting face cut at a predetermined angle. In this case, the target surface 124 may be formed on the cutting face.

The radiation 98 emitted from the target surface 124 of the anode 123 may pass through the collimator 112.

The collimator 112 filters the radiation 98 emitted from the radiation tube 111 to adjust a direction and a range of the radiation 98 to some degrees. The collimator 112 may include an opening through which radiation irradiated in a direction or in a range passes, and a plurality of collimator blades that absorb radiation irradiated in different directions. A user may control an irradiation direction and a range of radiation by changing a location or size of the opening. The collimator blades may be fabricated with a material such as lead Pb that can absorb radiation.

The radiation 98 passed through the collimator 112 is irradiated on the subject 99, and radiation transmitted through the subject 99 arrives at the radiation detector 130.

Figure 4:
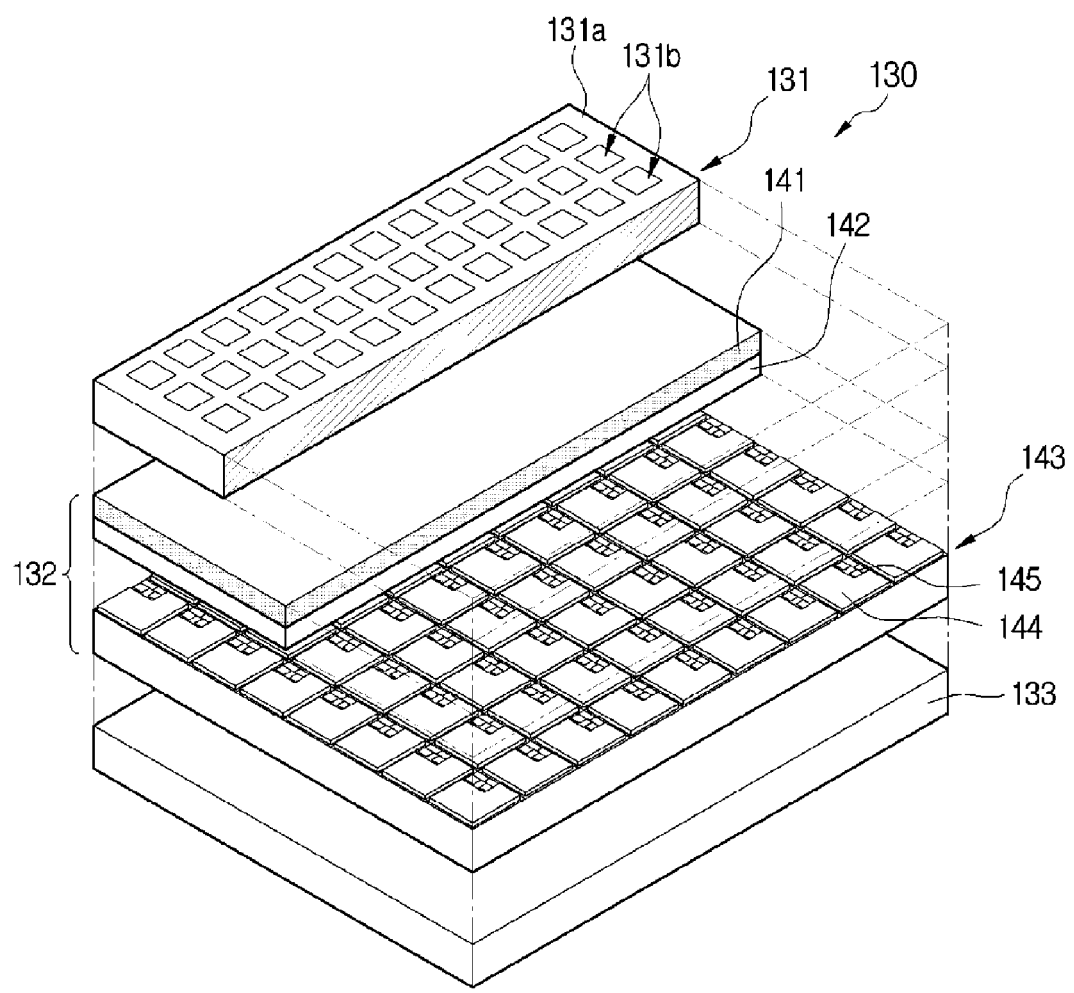
FIG. 4 is a view of a radiation detector of FIGS. 1 and 2.

FIG. 4 is a view of the radiation detector 130 of FIGS. 1 and 2.

Referring to FIG. 4, the radiation detector 130 includes the anti-scatter grid 131, the radiation detecting panel 132, and a PCB 133.

The anti-scatter grid 131 absorbs radiation passed through and scattered by the subject 99 to cause only radiation traveling in a proper direction to arrive at the radiation detecting panel 132. The anti-scatter grid 131 includes a plurality of partition walls 131*a* to block radiation, and a plurality of transmitting holes 131*b* through which radiation passes. The partition walls 131*a* may be made of a material such as lead Pb to absorb radiation scattered or refracted in the subject 99, and the transmitting holes 131*b* may pass radiation neither scattered nor reflected.

The radiation detecting panel 132 receives radiation, converts the received radiation into electrical signals corresponding to the radiation, and then outputs the electrical signals. The radiation detecting panel 132 may directly convert the radiation into the electrical signals (direct method). Alternatively, the radiation detecting panel 132 may generate visible light corresponding to the radiation, and then convert the visible light into the electrical signals (indirect method).

According to the direct method as shown in FIG. 4, the radiation detecting panel 132 includes a first electrode 141 to whose one surface radiation is incident, a semiconductor material layer 142 formed on another surface of the first electrode 141 to which no radiation is incident, and a flat plate 143 contacting the semiconductor material layer 142 that is opposite to the other surface of the first electrode 141, as shown in FIG. 4. On the flat plate 143, a plurality of second electrodes 144 and a plurality of thin film transistors 145 are arranged in one or more columns. The first electrode 141 may have positive (+) or negative (−) polarity, and the polarity of the second electrodes 144 may be opposite to that of the first electrode 1213. A predetermined bias voltage may be applied between the first electrode 141 and the second electrodes 144.

Electron-hole pairs created in the semiconductor material layer 142 according to incidence and absorption of radiation may move toward the first electrode 141 or the second electrodes 144 according to the polarities of the first electrode 141 and the second electrodes 144. The second electrodes 144 may receive holes or negative charges transferred from the semiconductor material layer 142, and output an electrical signal corresponding to the received negative charges. The thin film transistors 145 may read out electrical signals transferred from the corresponding second electrodes 144 to acquire image data. Each of the second electrodes 144 and the thin film transistors 145 corresponding to the second electrode 144 may be packaged in a CMOS chip.

If the radiation detecting panel 132 converts radiation into electrical signals according to the indirect method, a phosphor screen for outputting visible light corresponding to received radiation may be disposed between the anti-scatter grid 131 and the radiation detecting panel 132, and photo diodes, instead of the second electrodes 144, may be arranged on the flat plate 143 to convert visible light into electrical signals. Also, the radiation detecting panel 132 may include a scintillator configured to emit visible-light photons according to radiation, and photo diodes configured to detect the emitted visible-light photons.

According to an exemplary embodiment, the radiation detecting panel 132 may be a Photon Counting Detector (PCD).

The PCB 133 is disposed on another surface of the radiation detecting panel 132. The PCB 133 may be attached on the other surface of the radiation detecting panel 132 to control various operations of the radiation detecting panel 132 or to store image data output from the radiation detecting panel 132.

Electrical signals output from the radiation detector 130 may be temporarily or non-temporarily stored in a memory device such as a semiconductor storage provided on the substrate 133, and then transferred to the image processor 210. Also, image data acquired by the radiation detector 130 may be transferred directly to the image processor 210.

Figure 5:
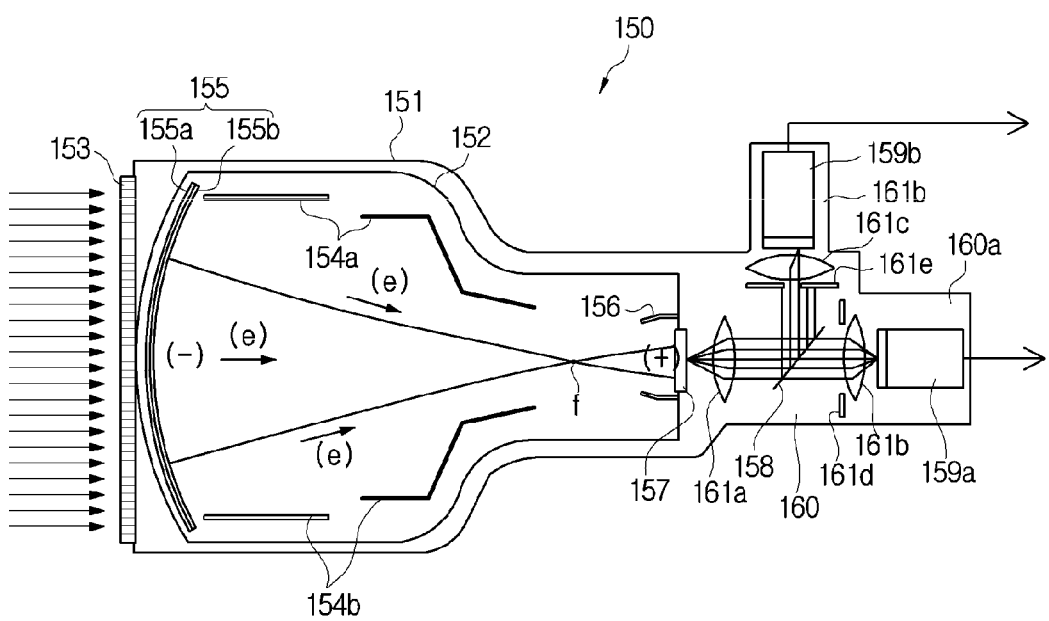
FIG. 5 is a view of an image intensifier according to an exemplary embodiment.

FIG. 5 is a view of the image intensifier 150 accordingly to an exemplary embodiment.

The radiation detector 130 of FIGS. 1 and 2 may include the image intensifier 150, instead of the radiation detecting panel 132 of FIGS. 1 and 4. The image intensifier 150 emits photons corresponding to incident radiation to thereby acquire image data.

Referring to FIG. 5, the image intensifier 150 includes a housing 151, a tube body 152, an anti-scatter grid 153, a radiation-electron converter 155, an anode 156, an electron-light converter 157, a light guide 160, and a plurality of lenses 161*a* to 161*c*.

The housing 151 accommodates the tube body 152, the anti-scatter grid 153, the radiation-electron converter 155, the anode 156, the electron-light converter 157, the light guide 160, and the lenses 161*a* to 161*c*, and fixes the above-mentioned devices stably while protecting them against an external impact. The housing 151 may be shaped to correspond to the shape of the tube body 152 or the light guide 160.

The tube body 152 causes electrons e traveling in the tube body 152 to be focused toward the anode 156, while stably fixing various components, such as the radiation-electron converter 155, the anode 156, and the electron-light converter 157. Also, the tube body 152 may prevent the electrons e from leaking out.

The tube body 152 may have a nearly cylindrical shape. The tube body 152 may be fabricated in a shape of a cylinder, wherein a diameter of a negative (−) polarity part of the tube body 152 in which the radiation-electron converter 155 is disposed is greater than a diameter of a positive (+) polarity part of the tube body 152 in which the electron-light converter 157 is disposed, as shown in FIG. 5. The negative (−) polarity part of the tube body 152 in which the radiation-electron converter 155 is disposed may be in the shape of a convex lens protruding in a direction in which radiation is incident.

The anti-scatter grid 153 is disposed at one end of the tube body 152 to which radiation is irradiated, and absorbs radiation passed through and scattered by a subject to cause only radiation traveling in a proper direction to arrive at the radiation-electron converter 155. The anti-scatter grid 153 may include a plurality of partition walls that are made of a material such as lead Pb and block radiation, and a plurality of transmitting holes through which non-scattered radiation passes. Radiation passed through the transmitting holes may arrive at the radiation-electron converter 155.

In the tube body 152, a plurality of focusing electrodes 154a and 154b are further disposed. In an inside of the tube body 152, electrons e may move to the anode 156, and be focused at a focusing point f that is a location near the anode 156. The focusing electrodes 154a and 154b induce the electrons e moving to the anode 156 to be focused at the focusing point f.

The radiation-electron converter 155 is disposed in the negative (−) polarity part of the tube body 152. The radiation-electron converter 155 includes a phosphor plate 155a configured to emit photons corresponding to incident radiation, and a photocathode 155b configured to emit electrons e corresponding to photons emitted from the phosphor plate 155a.

The anode 156 decides a movement direction and speed of electrons e. Electrons e move to the anode 156 according to their polarities, and are focused around the anode 156. The anode 156 may accelerate the moving electrons e.

The electron-light converter 157 is disposed around the anode 156. The electron-light converter 157 emits visible-light photons corresponding to the incident electrons e to an inside of the light guide 160. The electron-light converter 157 may include an output phosphor. Light emitted to the inside of the light guide 160 are refracted by the first lens 161a to travel in parallel. The output photons are received by first and second photographing units 159a and 159b, and the first and second photographing units 159a and 159b output and store electrical signals corresponding to the received photons to acquire image data.

A reflector 158 for reflecting the emitted photons in all directions is provided in the light guide 160. The reflector 158 transfers a part of the output photons to a first light guide 160a in which the first photographing unit 159 is disposed, and a remaining part of the output photons to a second light guide 160b in which the second photographing unit 159b is disposed. Accordingly, a plurality of image data may be acquired.

In the first light guide 160a and the second light guide 160b, the second lens 161b and the third lens 161c are respectively disposed to focus light. Light focused by the second lens 161b and the third lens 161c is transferred to the first photographing unit 159a and the second photographing unit 159b, respectively. In the first light guide 160a and the second light guide 160b a first diaphragm 161d and a second diaphragm 161e are respectively disposed to adjust amounts of light that are incident to the first photographing unit 159a and the second photographing unit 159b.

The first and second photographing units 159a and 159b receive photons, and then create and store electrical signals corresponding to the received photons to acquire image data. Each of the first and second photographing units 159a and 159b may include an image sensor having a plurality of image pickup devices, wherein each image pickup device may be a Charge-Coupled Device (CCD) or a Complementary Metal-Oxide Semiconductor (CMOS).

So far, an example of the radiography apparatus 1 has been described. However, the radiography apparatus 1 is not limited to the radiography apparatus 1 as described above. For example, the radiography apparatus 1 can be applied to Computed Tomography (CT), Full Field Digital Mammography (FFDM), or Single-Photon Emission Computed Tomography (SPECT) in the same manner or through appropriate modifications.

Hereinafter, operations of the image processor 210 will be described in more detail with reference to FIGS. 6 to 21.

Figure 6:
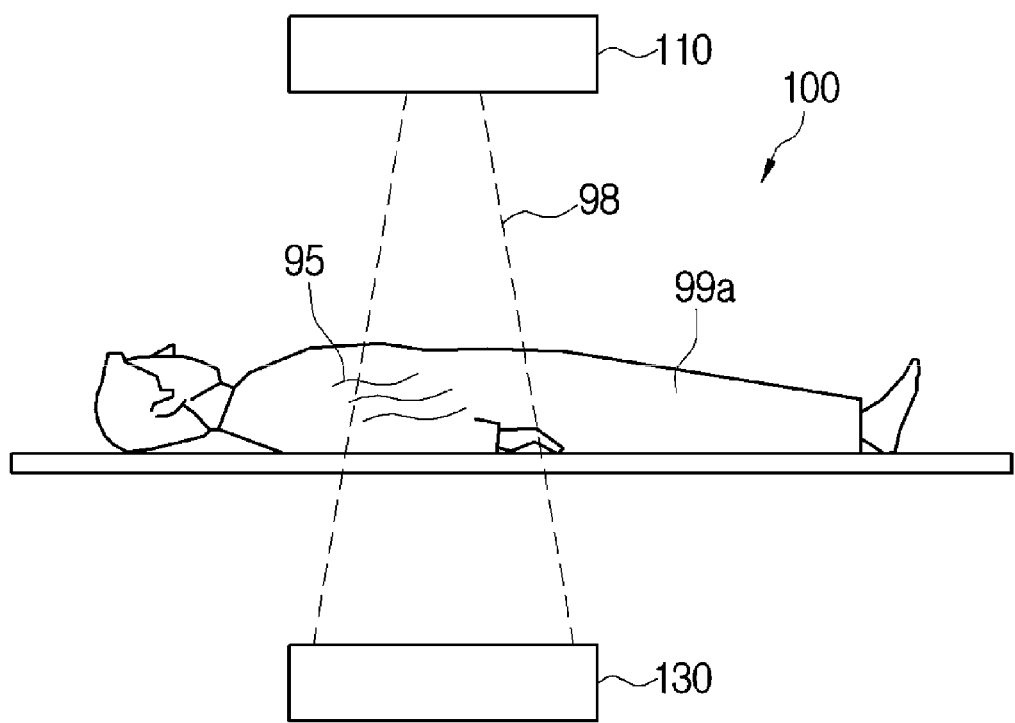
FIG. 6 is a view of scanning before a contrast agent is injected according to an exemplary embodiment.
Figure 7:
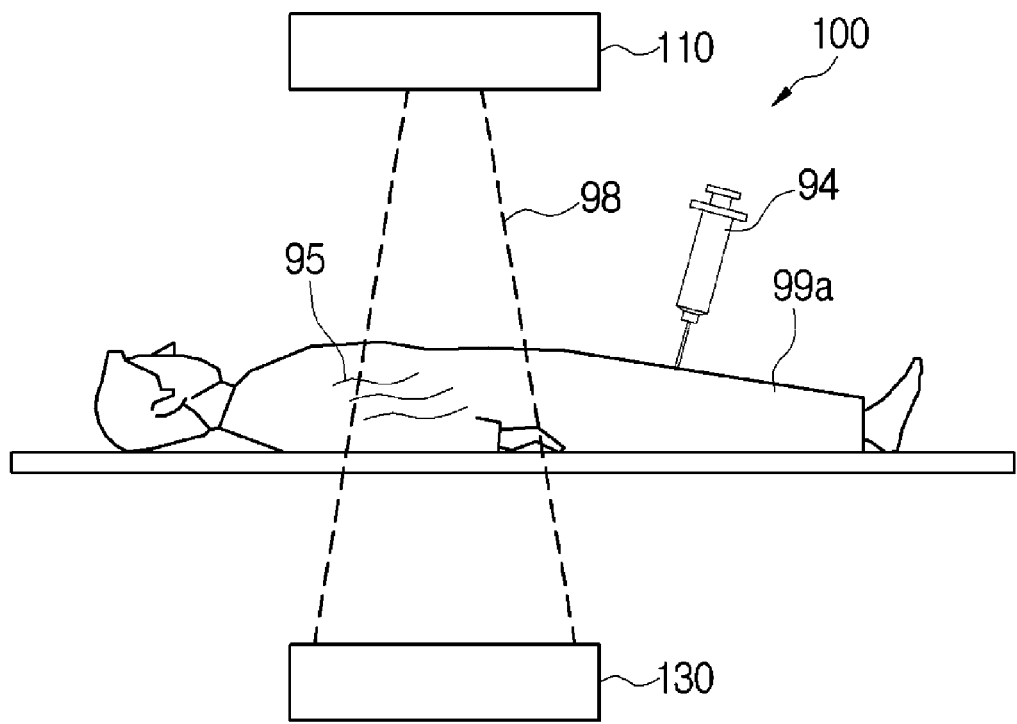
FIG. 7 is a view of scanning after a contrast agent is injected according to an exemplary embodiment.

FIG. 6 is a view of scanning before a contrast agent is injected according to an exemplary embodiment, and FIG. 7 is a view of scanning after a contrast agent is injected according to an exemplary embodiment.

As shown in FIG. 6, the radiographer 100 performs radiography on a human body 99a, which is a subject. In this case, the radiography may be performed before a contrast agent (94 of FIG. 7) is injected into the human body 99a. In detail, the radiation irradiator 110 irradiates the radiation 98 toward the human body 99a. The radiation detector 130 receives radiation transmitted through the human body 99a, and outputs electrical signals corresponding to the received radiation. The first processor 211 of the image processor 210 (see FIG. 1) may acquire a radiation image based on the electrical signals. Hereinafter, the radiation image acquired by the radiography performed before the contrast agent 94 is injected will be referred to as a first radiation image.

In this case, because attenuation coefficients of blood vessels 95 distributed in the human body 99a are not greatly different from those of muscles around the blood vessels 95, the blood vessels 95 may not be distinguished in the acquired radiation image.

As shown in FIG. 7, the radiographer 100 performs radiography after the contrast agent 94 is injected into the human body 99a. The contrast reagent 94 means a material that is injected into the inside of the human body 99a to increase a contrast of a material existing in the inside of the human body 99a. The contrast reagent 94 is used to clearly distinguish a material (for example, tissues or blood vessels) from other tissues during radiography. The contrast reagent 94 may increase a contrast of a material in the human body 99a by artificially increasing or decreasing a degree at which an internal material of the human body 99a transmits radiation. Accordingly, when the contrast agent 94 is used, a living body structure, lesions. etc. can be clearly distinguished from other materials around them, which can lead to accurate diagnosis of the subject 99.

The contrast reagent 94 may be iodine, iodine-gadolinium, or barium sulfate ($BaSO_4$). Also, the contrast reagent 94 may be a gas such as carbon oxide. One kind of contrast reagent 94 or a plurality of kinds of contrast reagents 94 may be injected into the human body 99a.

The contrast reagent 94 may be injected into the blood vessels 95 in the human body 99a through an arterial vessel located in the thigh, etc. of the human body 99a. The contrast reagent 94 may flow through the blood vessels 95 to increase the attenuation coefficient of the blood vessels 95. Accordingly, if radiography is performed after the contrast reagent 94 is injected, the blood vessels 95 can more clearly appear on a radiation image than before the contrast reagent 94 is injected. Hereinafter, a radiation image acquired by radiography performed after the contrast reagent 94 is injected will be referred to as a second radiation image. The first radiation image and the second radiation image may be photographed images of the same part (for example, the heart or brain) in the human body 99a.

FIG. 8A is a diagram of a process of acquiring a difference image accordingly to an exemplary embodiment.

As shown in FIGS. 6, 7, and 8A, if a first radiation image A acquired before the contrast reagent 94 is injected and a second radiation image B acquired after the contrast reagent 94 is injected are obtained, the second processor 212 of the image processor 210 (see FIG. 1) acquires a difference image C between the first radiation image A and the second radiation image B. In this case, the second processor 212 acquires the difference image C using a method of subtracting the first radiation image A from the second radiation image B (S1).

Because the second radiation image B is an image acquired after the contrast reagent 94 is injected, and the contrast reagent 94 flows through blood vessels 95a of the first radiation image A, only the blood vessels 95 may clearly appear on the difference image C between the first radiation image A and the second radiation image B. As such, by acquiring the difference image C, the radiography apparatus 1 may perform Digital Subtraction Angiography (DSA).

Figure 8B:
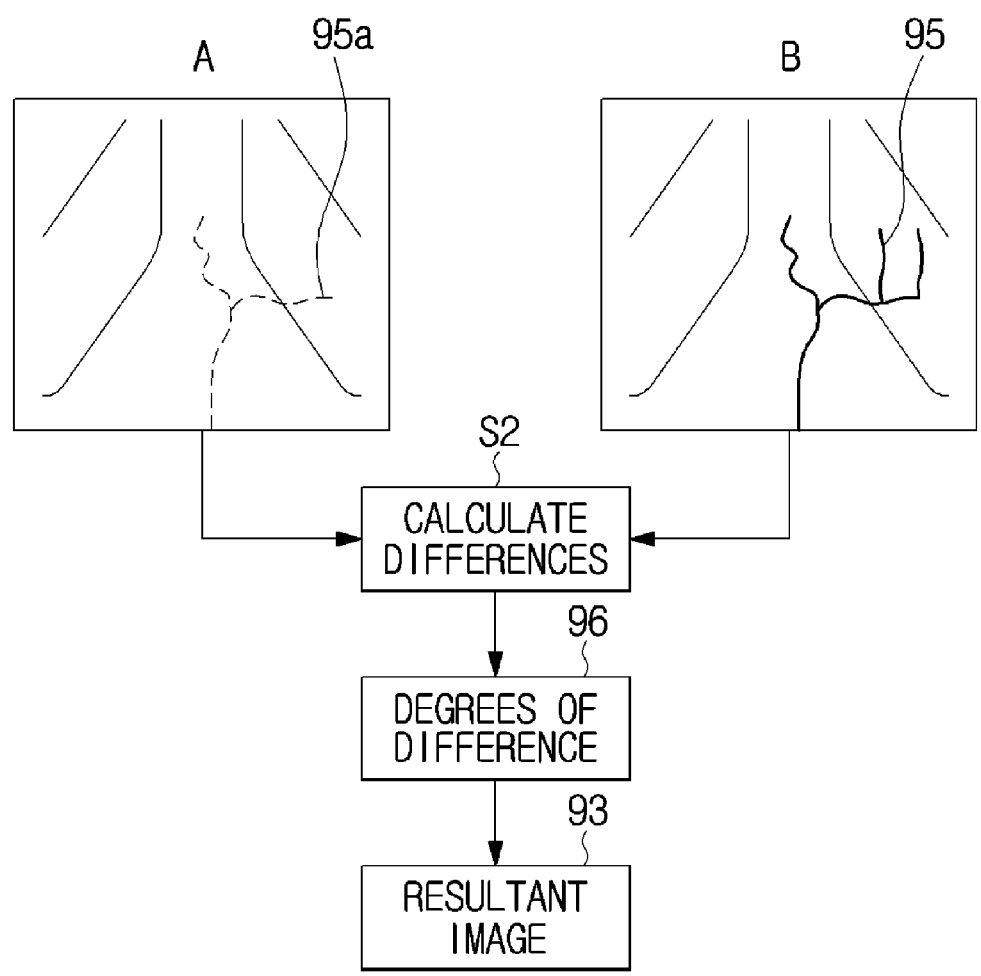
FIG. 8B is a diagram of a process of calculating differences between images using an image acquired before a contrast agent is injected and an image acquired after a contrast agent is injected according to an exemplary embodiment.

FIG. 8B is a diagram of a process of calculating differences between images using an image acquired before the contrast agent 94 is injected and an image acquired after the contrast agent 94 is injected accordingly to an exemplary embodiment.

Although the difference image C is acquired, if the human body 99a moves during radiography, a difference is made even in an area other than the blood vessels 95 between the first radiation image A and the second radiation image B according to the movement of the human body 99a, so that an artifact may be generated in the difference image C.

To compensate for the artifact, the third processor 213 (see FIG. 1) calculates and acquires data representing differences between the first radiation image A and a pixel of the second radiation image B, independently from acquiring the difference image C (S2).

Hereinafter, for convenience of description, various data including degrees (or values) representing differences between all pixel values of the first radiation image A and a pixel value of the second radiation image B will be referred to as degrees of difference 96.

After calculating the degrees of difference 96, the third processor 213 acquires a resultant image 93 using the degrees of difference 96. The resultant image 93 means an image that is acquired by image processing of the image processor 210 and can be displayed for a user through the display 202 (see FIG. 1). According to exemplary embodiments, the image processor 210 may further perform image processing on the resultant image 93 to correct the resultant image 93. The corrected resultant image 93 may be displayed for a user through the display 202.

In detail, the third processor 213 may calculate differences between a pixel value of an arbitrary pixel of the second radiation image B and pixel values of all pixels of the first radiation image A, and acquire the degrees of differences 96 between the first radiation image A and a selected pixel of the second radiation image B using the calculated differences. The process of acquiring the degrees of difference 96 may be performed on all pixels of the second radiation image B. Herein, data related to the pixels of the first radiation image A and the second radiation image B may be at least one among pixel intensities, values acquired by edge detection, values acquired by wavelet transform, and wavelet coefficients.

Hereinafter, the process of calculating the degrees of difference 96 will be described in more detail.

Figure 9:
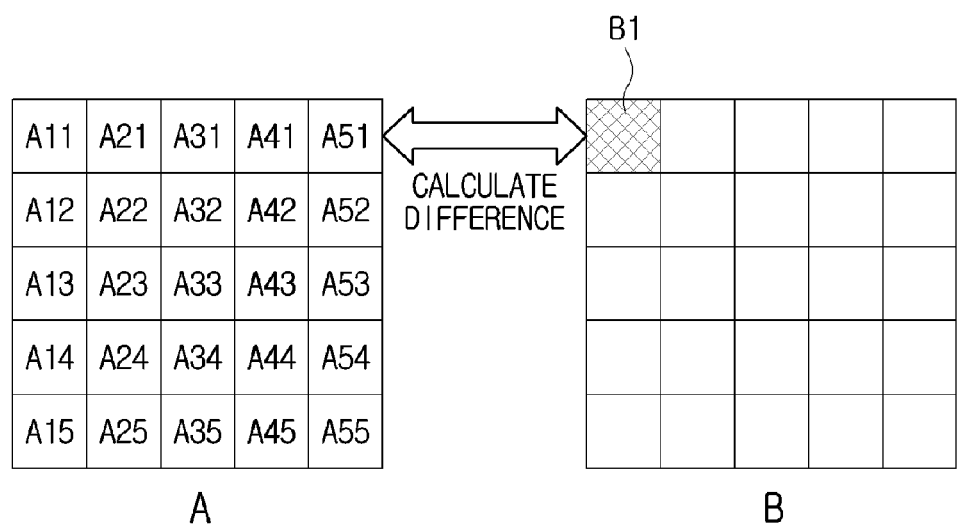
FIG. 9 is a diagram of a method of calculating a difference between a pixel of a first radiation image and an arbitrary pixel of a second radiation image according to an exemplary embodiment.
Figure 11:
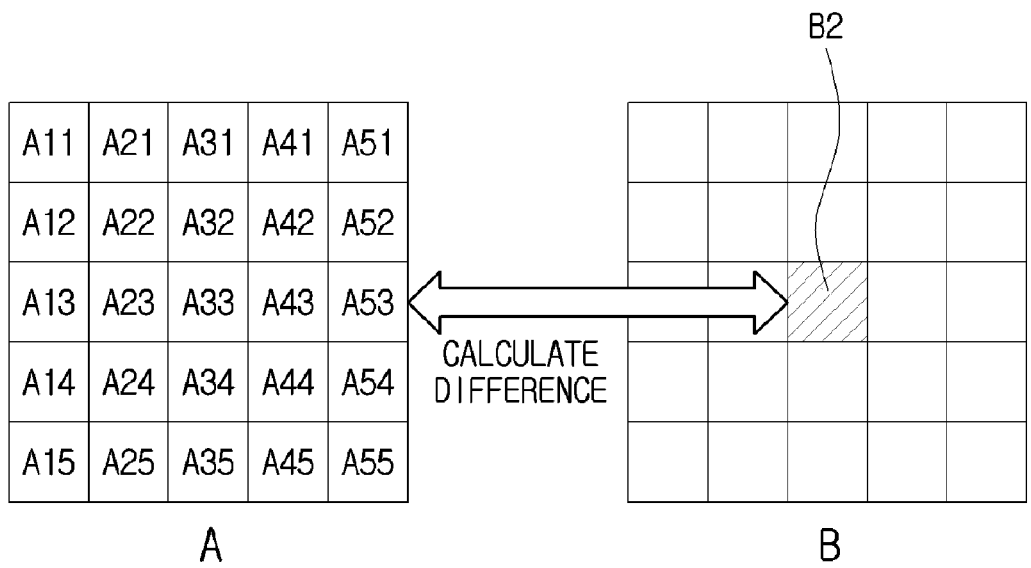
FIG. 11 is a diagram of a method of calculating a difference between a pixel of a first radiation image and an arbitrary pixel of a second radiation image according to another exemplary embodiment.

FIG. 9 is a diagram of a method of calculating a difference between a pixel of a first radiation image and an arbitrary pixel of a second radiation image according to an exemplary embodiment, and FIG. 10 is a table used in the method of FIG. 9. FIG. 11 is a diagram of a method of calculating a difference between a pixel of a first radiation image and an arbitrary pixel of a second radiation image according to another exemplary embodiment, and FIG. 12 is a table used in the method of FIG. 11

In the tables shown in FIGS. 10 and 12, data of a first radiation image A means pixel intensities of individual pixels of the first radiation image A, and data of a second radiation image B means a pixel intensity of an arbitrary pixel selected from the second radiation image B. However, the pixel intensities shown in the tables of FIGS. 10 and 12 have been decided for convenience of description, and may be different from experimental values.

As shown in FIG. 9, the third processor 213 selects an arbitrary pixel B1 of the second radiation image B, and calculates differences between a pixel value of the arbitrary pixel B1 and pixel values of all pixels A11 to A55 of the first radiation image A. In this case, the pixel values may be pixel intensities given as any values between 0 and 255. However, values acquired by edge detection, values acquired by wavelet transform, or wavelet coefficients may be used instead of pixel intensities, as described above.

For example, as shown in FIG. 10, the pixel value of the arbitrary pixel B1 of the second radiation image B is 100, and the third processor 213 calculates differences between the pixel value 100 of the arbitrary value B1 and the pixel values of the individual pixels A11 to A55 of the first radiation image A.

After calculating the differences between the pixel value of the arbitrary pixel B1 of the second radiation image B and the pixel values of all the pixels A11 to A55 of the first radiation image A, the third processor 213 may acquire one of the degrees of difference 96 between the first radiation image A and the pixel B1 of the second radiation image B based on the calculated differences.

According to an exemplary embodiment, the third processor 213 may decide the smallest or greatest value of the differences between the pixel value of the arbitrary pixel B1 of the second radiation image B and the pixel values of all the pixels A11 to A55 of the first radiation image A, as one of the degrees of difference 96 between the first radiation image A and the second radiation image B. For example, the third processor 213 may decide "2", which is a difference between the pixel value of the pixel B1 of the second radiation image B and the pixel value of the pixel A55 of the first radiation image A, as one of the degrees of difference 96 between the first radiation image A and the second radiation image B, as shown in FIG. 10.

Also, according to another exemplary embodiment, the third processor 213 may square the acquired differences, sum the squared values, and then calculate a radical root of the summed result to thereby acquire one of the degrees of difference 96. In this case, the third processor 213 may acquire one of the degrees of difference 96 according to Equation (2) below.

$$R_k = \sqrt{\Sigma_{ij}(X_{ij} - Y_k)^2},\qquad(2)$$

where $R_k$ represents a degree of difference between the first radiation image A and the pixel of the second radiation image B, i and j are indexes for identifying each pixel of the first radiation image A, k is an index for identifying an arbitrary pixel of the second radiation image B, $X_{ij}$ represents a pixel value of a pixel corresponding to the indexes ij of the first radiation image A, and $Y_k$ represents a pixel value of an arbitrary pixel $B_k$ of the second radiation image B.

Also, accordingly to another exemplary embodiment, the third processor 213 may acquire one of the degrees of difference 96 by calculating an average value of the differences, or using one of various methods that can be considered by one of ordinary skill in the art.

As shown in FIGS. 11 and 12, the third processor 213 may acquire one of the degrees of difference 96 with respect to another pixel B2 of the second radiation image B, in the same manner. The process of calculating one of the degrees of difference 96 is performed on all pixels of the second radiation image B. Accordingly, the degrees of difference 96 is calculated for all the pixels of the second radiation image B.

If the arbitrary pixel B1 of the second radiation image B is a pixel in an area where none of the blood vessels 95 into which the contrast reagent 94 has been injected are displayed, the pixel value of the arbitrary pixel B1 may be identical to the pixel values of the pixels A11 to A55 of the first radiation image A, or may have a small difference within a predetermined range from the pixel values of the pixels A11 to A55 of the first radiation image A. For example, the difference between the pixel value of the arbitrary pixel B1 of the second radiation image B and the pixel value of each pixel of the first radiation image A may be zero or an arbitrary value (for example, 1 or 2) close to zero, as shown in FIG. 10. Accordingly, a degree of difference of a small value may be acquired.

If the arbitrary pixel B2 of the second radiation image B is a pixel in an area where the blood vessels 95 into which the contrast reagent 94 has been injected are displayed, the pixel value of the arbitrary pixel B2 may be greatly different from the pixel values of the pixels A11 to A55 of the first radiation image A. For example, as shown in FIG. 12, if a pixel intensity of a pixel at which the blood vessels 95 into which the contrast reagent 94 has been injected are displayed is 100, and a pixel intensity of a pixel at which a material around the blood vessels 95 is displayed is a value close to zero, a difference between a pixel value of each pixel of the first radiation image A and the pixel value of the arbitrary pixel B2 of the second radiation image B may be 100 or a value close to 100. Accordingly, a degree of difference of a great value may be acquired.

According to another exemplary embodiment, the third processor 213 may decide an arbitrary threshold value, and compare the acquired degree of difference to the arbitrary threshold value to determine whether to discard the degree of difference for each pixel of the second radiation image B. If the third processor 213 determines that the acquired degree of difference is smaller than the arbitrary threshold value, the third processor 213 may discard the acquired degree of difference 96. If the third processor 213 determines that the acquired degree of difference is greater than the arbitrary threshold value, the third processor 213 may maintain the acquired degree of difference. Herein, the arbitrary threshold value may have been decided in advance by a user or a system designer. Also, the arbitrary threshold value may be decided according to the formula of calculating a degree of difference.

According to another exemplary embodiment, the third processor 213 may maintain all of the acquired degrees of difference 96, without discarding them. Because a pixel value of a pixel in an area into which no contrast reagent 94 has been injected shows no substantial difference from the pixel values of the pixels of the first radiation image A, the degree of difference may be zero or a value close to zero although all of the acquired degrees of difference 96 are maintained.

Figure 13A:
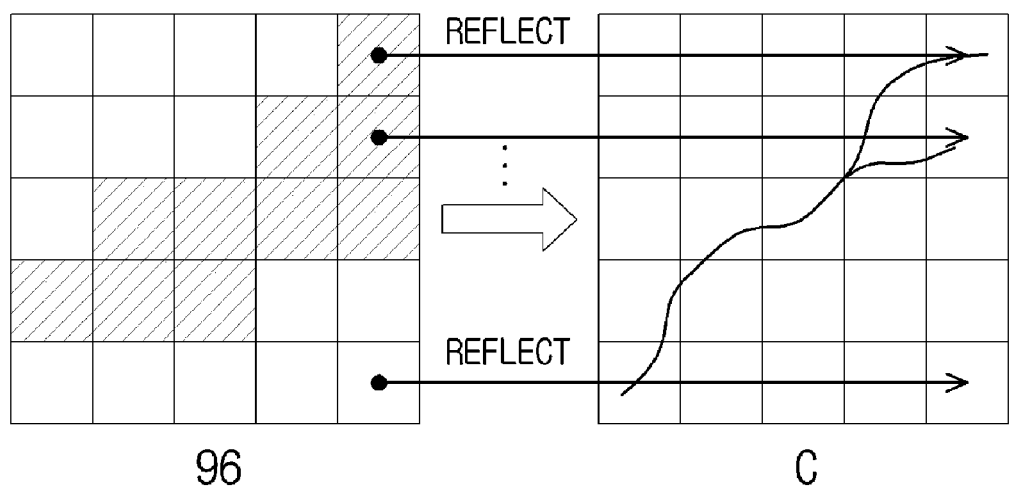
FIG. 13A is a diagram of a process of creating a resultant image using degrees of difference according to an exemplary embodiment.
Figure 13B:
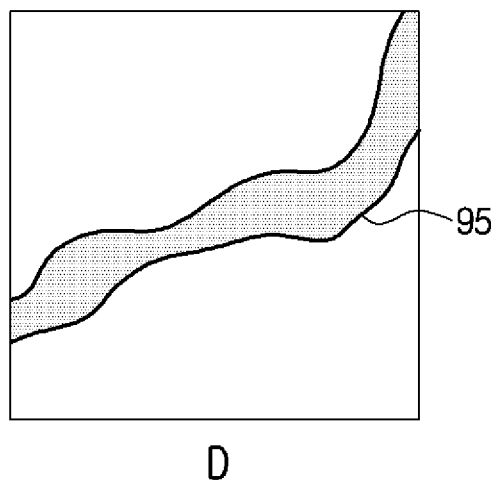
FIG. 13B is an example of the created resultant image of FIG. 13A.

FIG. 13A is a diagram of a process of creating a resultant image using degrees of difference according to an exemplary embodiment, and FIG. 13B is an example of the created resultant image of FIG. 13A.

Referring to FIGS. 13A and 13B, after the degrees of differences 96 for all the pixels of the second radiation image B are calculated, the third processor 213 creates a resultant image D using the degrees of difference 96 for all the pixels of the second radiation image B. In other words, the third processor 213 creates resultant image D using a group consisting the degrees of difference 96.

In detail, after the third processor 213 calculates the degrees of differences 96 for all pixels of the second radiation image B, the third processor 213 reflects the degrees of difference 96 to the difference image C acquired by the second processor 212 to correct the difference image C. Accordingly, the third processor 2134 acquires the first resultant image D.

The third processor 213 may select a pixel of the difference image C, decide a pixel of the second radiation image B corresponding to the selected pixel, and then acquire a degree of difference corresponding to the pixel of the second radiation image B. Herein, the pixel of the second radiation image B corresponding to the selected pixel means a pixel of the second radiation image B at a location corresponding to that of the selected pixel of the difference image C.

Successively, the third processor 213 may reflect the degree of difference to the selected pixel of the difference image C to correct the selected pixel of the difference image C, as shown in FIG. 13A. In this case, the third processor 213 may multiply a pixel value of the selected pixel by the degree of difference, or divide the product of the pixel value of the selected pixel and the degree of difference by a predetermined value, thereby correcting the selected pixel of the difference image C. According to another exemplary embodiment, the third processor 213 may further add a predetermined weight to apply the degree of difference to the pixel value of the selected pixel. The third processor 213 may apply the above-described process to all pixels of the difference image C to thereby correct the difference image C.

If the third processor 213 has discarded degrees of difference that are smaller than the threshold value, pixels of the difference image C corresponding to the discarded degrees of difference may not be corrected.

Because the greater degrees of difference 96 are acquired at the blood vessels 95 through which the contrast reagent 94 passes, and the difference image C displays only the blood vessels 95 through which the contrast reagent 94 passes, as described above, if the degrees of difference 96 are applied to the difference image C, the first resultant image D with the highlighted blood vessels 95 can be acquired.

Figure 14:
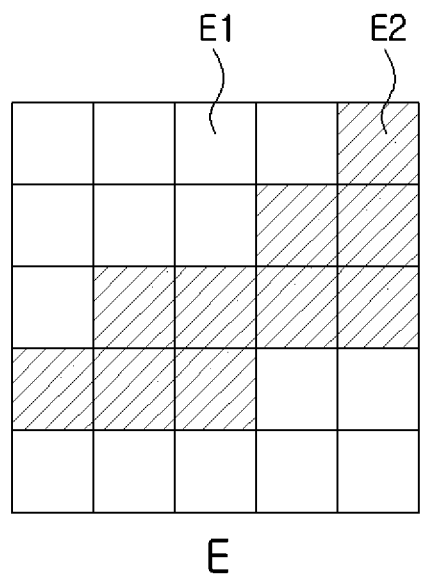
FIG. 14 is a diagram of a process of creating a resultant image using degrees of difference according to another exemplary embodiment.

FIG. 14 is a diagram of a process of creating a resultant image using degrees of difference according to another exemplary embodiment.

As shown in FIG. 14, the third processor 213 creates a second resultant image E using only the degrees of difference 96. In detail, the third processor 213 combines the degrees of difference 96 to create the second resultant image E. The third processor 213 locates the degrees of difference 96 at locations of the corresponding pixels to create an image E1 as shown in FIG. 14. In FIG. 14, the brighter areas E1 may represent areas at which the smaller degrees of difference 96 are located, and darker areas E2 may represent areas at which the greater degrees of difference 96 are located.

Because a great degree of difference is acquired from an area through which the contrast reagent 94 passes, and a small degree of difference is acquired from an area through which no contrast reagent 94 passes, as described above, the third processor 213 may represent the blood vessels 95 in the second resultant image E, like the difference image C. Accordingly, the second resultant image E acquired using the degrees of difference 96 may be used instead of the difference image C or the first resultant image D.

So far, the exemplary embodiments in which the third processor 213 acquires the first resultant image D and the second resultant image E by calculating the degrees of difference 96 without dividing the plurality of radiation images A and B have been described. In other words, the above-described processes are to acquire the first resultant image D and the second resultant image E using the first radiation image A and the second radiation image B. According to another exemplary embodiment, the third processor 213 may divide each of the first radiation image A and the second radiation image B into two areas or more, then acquire resultant images D and E for each area, and combine the resultant images D and E acquired for each area to thereby acquire a final resultant image.

Figure 15:
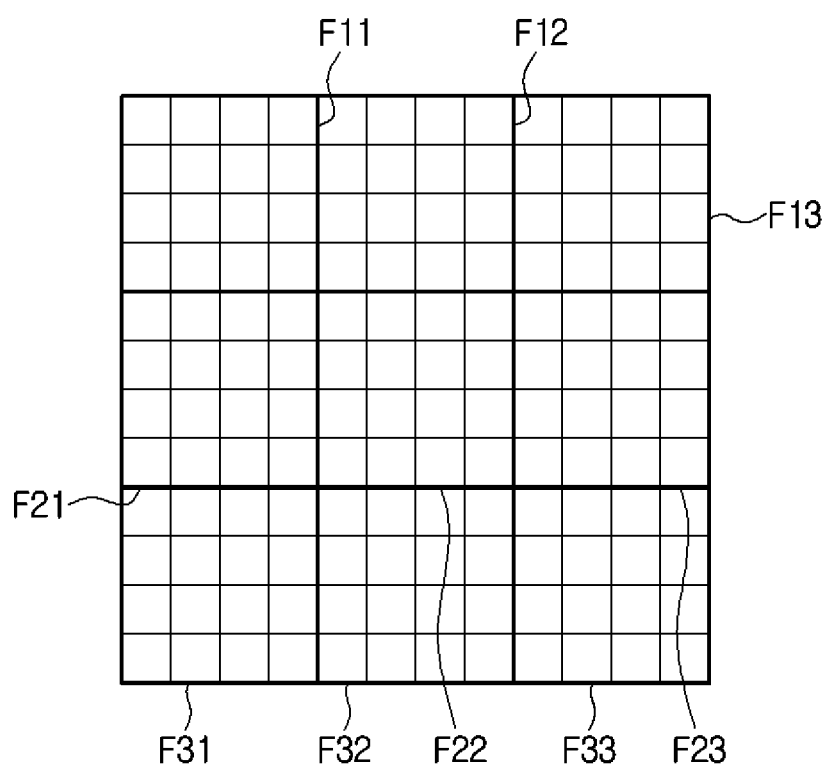
FIG. 15 is a diagram of area division that is performed on a first radiation image or a second radiation image according to a first exemplary embodiment.
Figure 16:
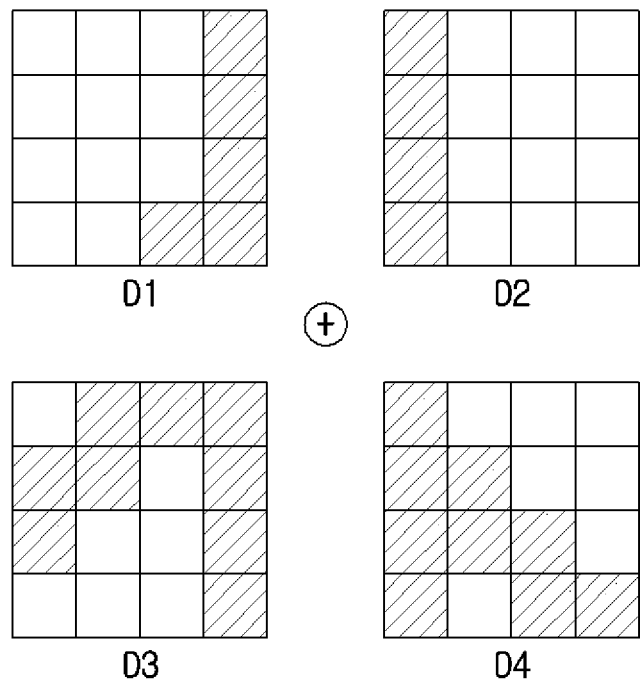
FIG. 16 is a diagram of a process of calculating differences for each area, and combining a plurality of areas for which differences are calculated according to the first exemplary embodiment.
Figure 17:
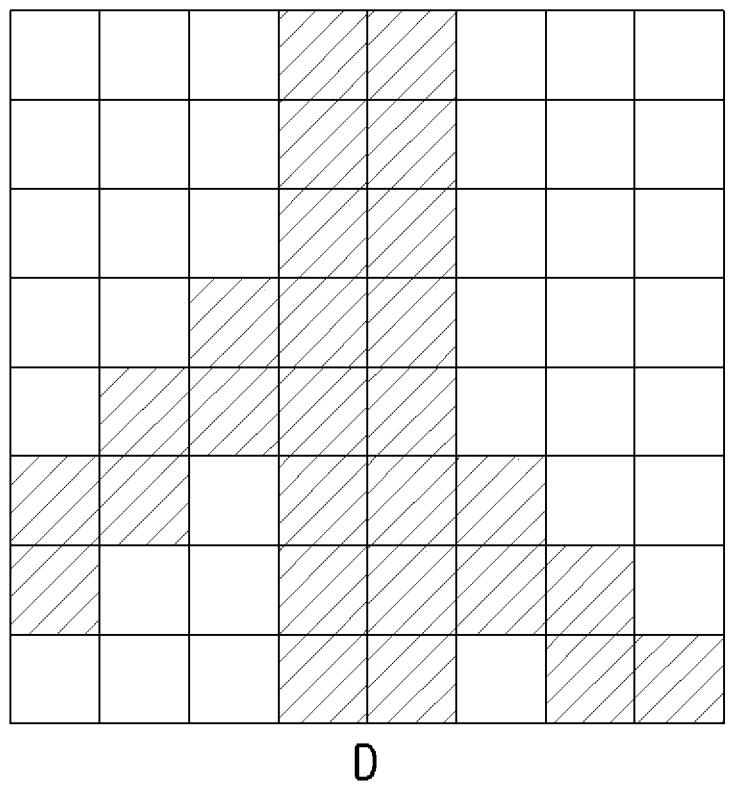
FIG. 17 is an example of a resultant image created by combining the areas according to the first exemplary embodiment.

FIG. 15 is a diagram of area division that is performed on a first radiation image or a second radiation image according to a first exemplary embodiment. FIG. 16 is a diagram of a process of acquiring differences for each area, and combining a plurality of areas for which differences are acquired according to the first exemplary embodiment. FIG. 17 is an example of a resultant image created by combining the areas according to the first exemplary embodiment.

As shown in FIG. 15, the third processor 213 divides the first radiation image A or the second radiation image B into a plurality of areas F11, F12, F13, F21, F22, F23, F31, F32, and F33 having the same size. Hereinafter, the areas F11, F12, F13, F21, F22, F23, F31, F32, and F33 will be referred to as divided areas F11 to F33.

Each of the divided areas F11 to F33 may be in a shape of a square or rectangle. The sizes or locations of the divided areas of the first radiation image A may be the same as those of the divided areas of the second radiation image B so that the divided areas of the first radiation image A correspond to the divided areas of the second radiation image B. The same size of two divided areas means that a length of a bottom side and a height of one of the two divided areas are the same as those of another one of the two divided areas, and different sizes of two divided areas mean that the length of the bottom side or the height of one of the two divided areas is different from that of another one of the two divided areas.

When the divided areas F11 to F33 have the same size, each of the divided areas F11 to F33 includes the same number of pixels as shown in FIG. 15.

The third processor 213 may calculate differences between pixel values of all pixels existing in a divided area of the first radiation image A and a pixel value of an arbitrary pixel of a divided area of the second radiation image B, and calculate a degree of difference for the arbitrary pixel in the divided area of the second radiation image B based on the calculated differences. In this case, the divided area of the second radiation image B may correspond to the divided area of the first radiation image A.

After the third processor 213 acquires degrees of differences for all pixels in the divided area of the second radiation image B, the third processor 213 may acquire a resultant image D for the divided area of the second radiation image B. The third processor 213 may apply the above-described process to the remaining divided areas of the second radiation image B in the same manner, to create resultant images D1 to D4 for all the divided areas F11 to F21 of the second radiation image B, as shown in FIG. 16. Thereafter, the third processor 213 may combine the resultant images D1 to D4 for the divided areas F11 to F21 to acquire a final resultant image D as shown in FIG. 17.

Because each of the first radiation image A and the second radiation image B is divided into a plurality of areas, data (for example, pixel intensity distribution) of pixels in each divided area may not greatly change although the subject 99, for example, the human body 99a, moves during radiography. Accordingly, through the area division, the relatively more accurate resultant image D can be acquired.

Figure 18:
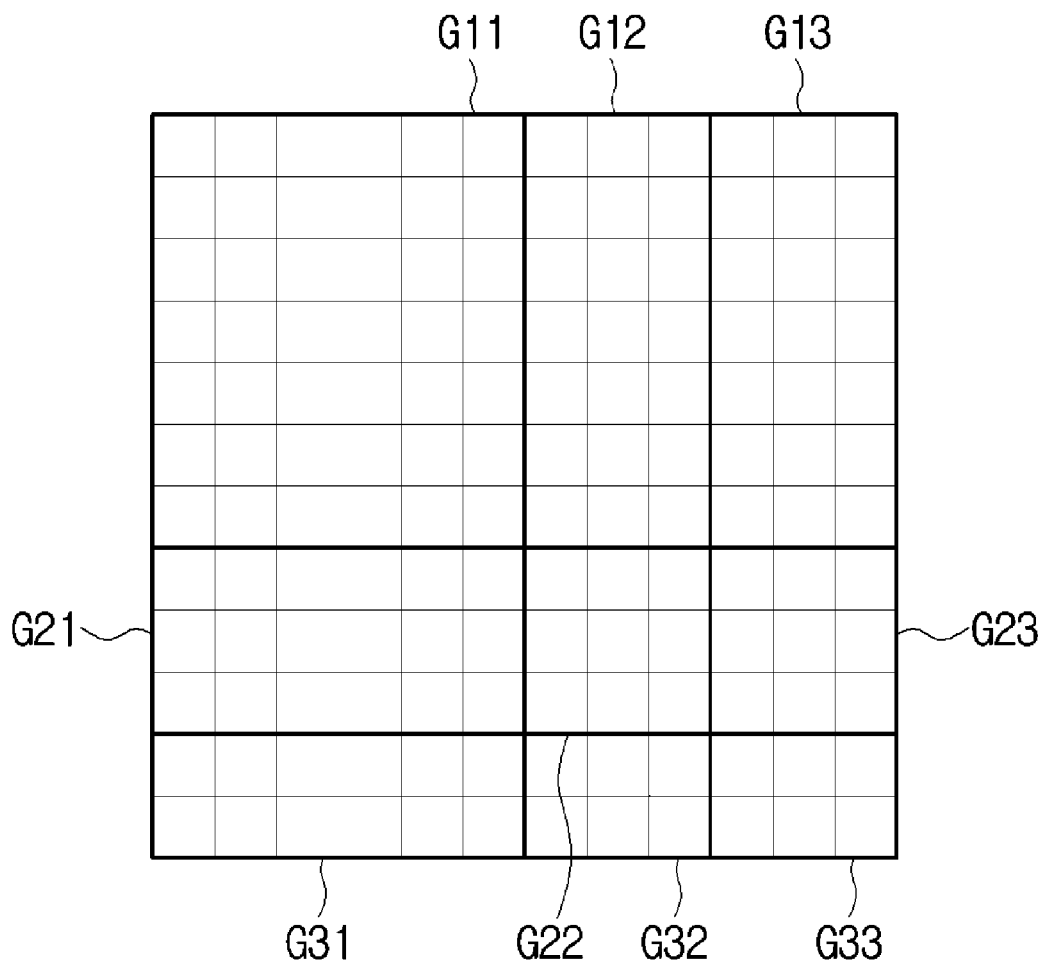
FIG. 18 is a diagram of area division that is performed on a first radiation image or a second radiation image according to a second exemplary embodiment.

FIG. 18 is a diagram of area division that is performed on a first radiation image or a second radiation image according to a second exemplary embodiment.

The third processor 213 divides the first radiation image A or the second radiation image B into a plurality of divided areas G11 to G33 that have different shapes or sizes, as shown in FIG. 18. Also, the third processor 213 may divide an area of the first radiation image A or the second radiation image B into a plurality of divided areas having different shapes or sizes, and a remaining area of the first radiation image A or the second radiation image B into a plurality of divided areas having the same shape or size. In other words, at least one of a plurality of divided areas of the first radiation image A or the second radiation image B may have a size that is different from that of the remaining divided areas. The third processor 213 may calculate a degree of difference for each divided area, and combine resultant images of the divided areas acquired according to results of the calculation to thereby acquire a final resultant image.

Figure 19:
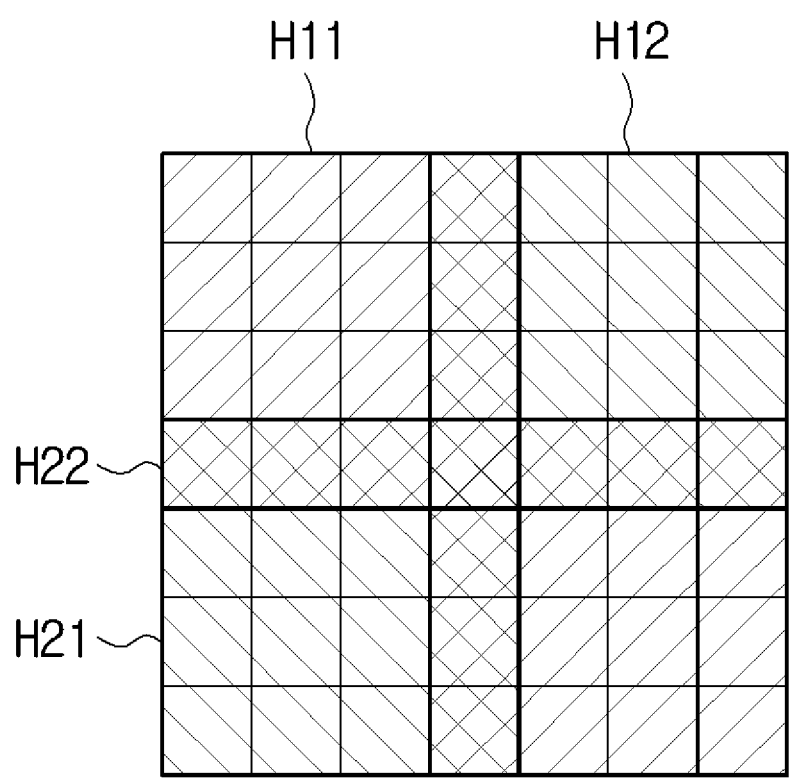
FIG. 19 is a diagram of area division that is performed on a first radiation image or a second radiation image according to a third exemplary embodiment.

FIG. 19 is a diagram of area division that is performed on a first radiation image or a second radiation image according to a third exemplary embodiment.

The third processor 213 divides an image into a plurality of divided areas H11 to H22 such that at least two of the divided areas H11 to H22 overlap each other. According to exemplary embodiments, all of the divided areas H11 to H22 may overlap each other. Accordingly, at least two of the divided areas H11 to H22 include an overlapping part. The overlapping divided areas H11 to H22 share one or more pixels. The overlapping divided areas H11 to H22 may have the same size or shape, or different sizes or shapes. Also, some of the overlapping divided areas H11 to H22 may have the same size or shape. The third processor 213 may calculate a degree of difference for each divided area, and combine resultant images of the divided areas acquired according to results of the calculation to thereby acquire a final resultant image.

Figure 20:
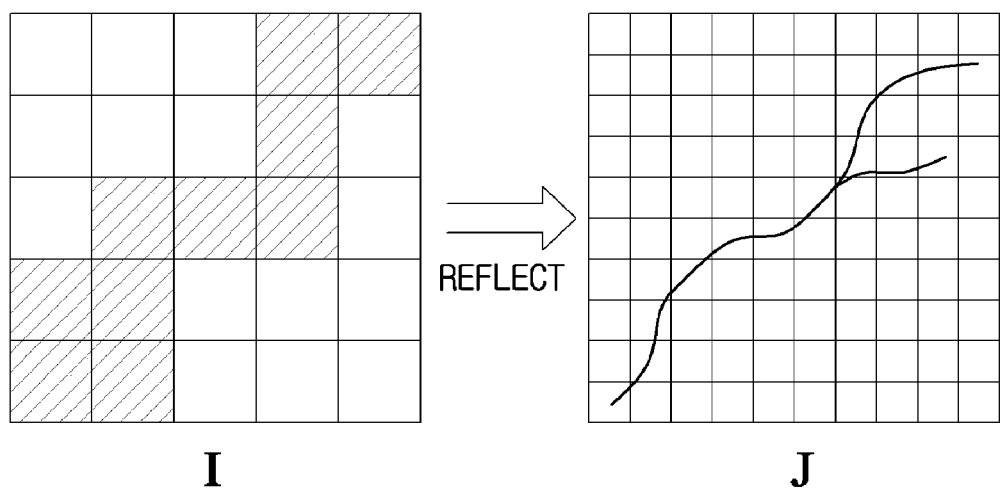
FIG. 20 is a diagram of a multi-resolution method according to an exemplary embodiment.

FIG. 20 is a diagram of a multi-resolution method according to an exemplary embodiment.

An image may be represented with a predetermined resolution. Herein, the resolution means an index indicating a number of pixels forming an image. The resolution can be represented by a number of pixels existing in a unit length. For example, the resolution may be represented in units of pixels per inch (ppi) representing a number of pixels per inch. As an image has a higher resolution, the image can be implemented with more data, and accordingly, the image may include more information.

An image of a predetermined resolution may be converted into an image of another resolution. For example, an image of a high resolution may be converted into an image of a low resolution, which is called down-sampling. In contrast, an image of a low resolution may be converted into an image of a high resolution, which is called up-sampling. The down-sampling and the up-sampling may be performed by various kinds of transform functions. For example, the down-sampling may acquire an image of a lower resolution by converting a plurality of pixels of an image into a pixel to reduce the number of pixels. In this case, a pixel value of a pixel of the image of the lower resolution may be decided as a mean value of the pixel values of the plurality of pixels or as any one of the pixel values of the plurality of pixels. The multi-resolution method is to perform image processing on an image of a low resolution and to then reflect a result of the image processing to an image of a high resolution corresponding to the image of the low resolution, to increase image processing speed.

As shown in FIG. 20, the third processor 213 calculates degrees of difference I of a second radiation image using a first radiation image of a low resolution and a second radiation image of a low resolution. Because the first radiation image of the low resolution and the second radiation image of the low resolution have a relatively smaller number of pixels, it is possible to reduce an amount of calculation. When the degrees of difference I are acquired using the first radiation image of the low resolution and the second radiation image of the low resolution, the third processor 213 applies the degrees of difference I to a difference image J between a first radiation image of a high resolution and a second radiation image of a high resolution to acquire a new resultant image. For example, the third processor 213 may apply a degree of difference corresponding to a pixel of the low resolution to a plurality of pixels of the difference image J acquired with a high resolution to thereby acquire the new resultant image.

Hereinafter, various exemplary embodiments of a method of controlling a radiography apparatus will be described with reference to FIGS. 21 to 24.

Figure 21:
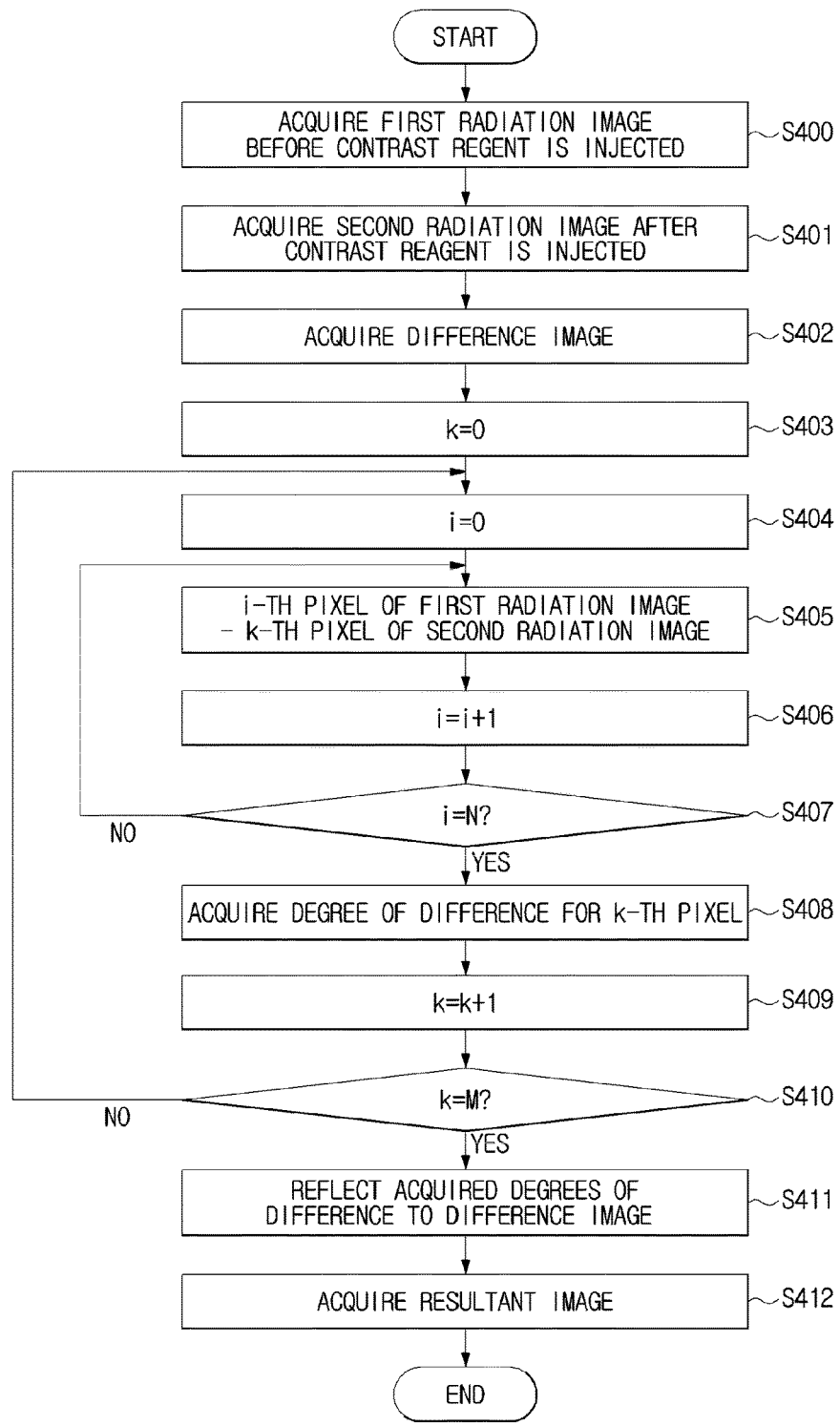
FIG. 21 is a flowchart illustrating a method of controlling a radiography apparatus according to a first exemplary embodiment.

FIG. 21 is a flowchart illustrating a method of controlling a radiography apparatus according to a first exemplary embodiment.

As shown in FIG. 21, in operation S400, before a contrast regent is injected into a subject, radiation is irradiated to the subject, radiation transmitted through the subject is received, and electrical signals corresponding to the received radiation are converted and combined to acquire a first radiation image of the subject.

In operation S401, after a contrast reagent is injected to the subject, and after a predetermined time elapses, radiation is again irradiated to the subject to acquire a second radiation image of the subject. In this case, because the contrast reagent injected into the subject may move through blood vessels inside the subject, the second radiation image may show the blood vessels more clearly.

In operation S402, after the first radiation image and the second radiation image are acquired, subtraction is performed on the first radiation image and the second radiation image to acquire a difference image between the first radiation image and the second radiation image. Operation S402 of acquiring the difference image may be performed when operations S403 to S410, which will be described later, are performed, or after operations S403 to S410 are performed.

In operations S403 to S405, after the first radiation image and the second radiation image are acquired, a difference between a pixel value of a first or i-th pixel of the first radiation image and a pixel value of a first of k-th pixel of the second radiation image is calculated.

In operation S406, a value of i is iterated so that a difference between a pixel value of a second or i+1-th pixel of the first radiation image and a pixel value of a second or i+1-th pixel of the second radiation image is calculated. Operations S403 to S406 are performed until all of N pixels of the first radiation image are processed.

In operation S407, it is determined whether the value of i is equal to a number N of the pixels of the first radiation image. When the value of i is determined to be equal to the number N of the pixels of the first radiation image, the method continues in operation S408. Otherwise, the method returns to operation S405. According to exemplary embodiments, values acquired by edge detection or wavelet coefficients may be used instead of pixel values.

In operation S408, a degree of difference for the first or k-th pixel of the second radiation image is acquired. The degree of difference means a value representing a difference between all the pixels of the first radiation image and the corresponding pixel of the second radiation image. The degree of difference may be the smallest value of the calculated differences, or as a radical root of a sum of squares of a difference between the pixel value of each pixel of the first radiation image and the pixel value of the first or k-th pixel of the second radiation image. However, the degree of difference may be acquired by one of various methods that can be considered by one of ordinary skill in the art.

In operation S409, a value of k is iterated so that operations S403 to S408 are performed on a second or k+1-th pixel of the second radiation image to calculate a degree of difference for the second or k+1-th pixel of the second radiation image. Operations S403 to S408 are performed on all of M pixels of the second radiation image.

In operation S410, it is determined whether the value of k is equal to a number M of the pixels of the second radiation image. When the value of k is determined to be equal to the number M of the pixels of the second radiation image, the method continues in operation S411. Otherwise, the method returns to operation S404. As a result, degrees of difference for all the pixels of the second radiation image are acquired.

In operation S411, the acquired degrees of difference are reflected to the difference image to correct the difference image. Accordingly, in operation S412, a new resultant image is acquired.

Figure 22:
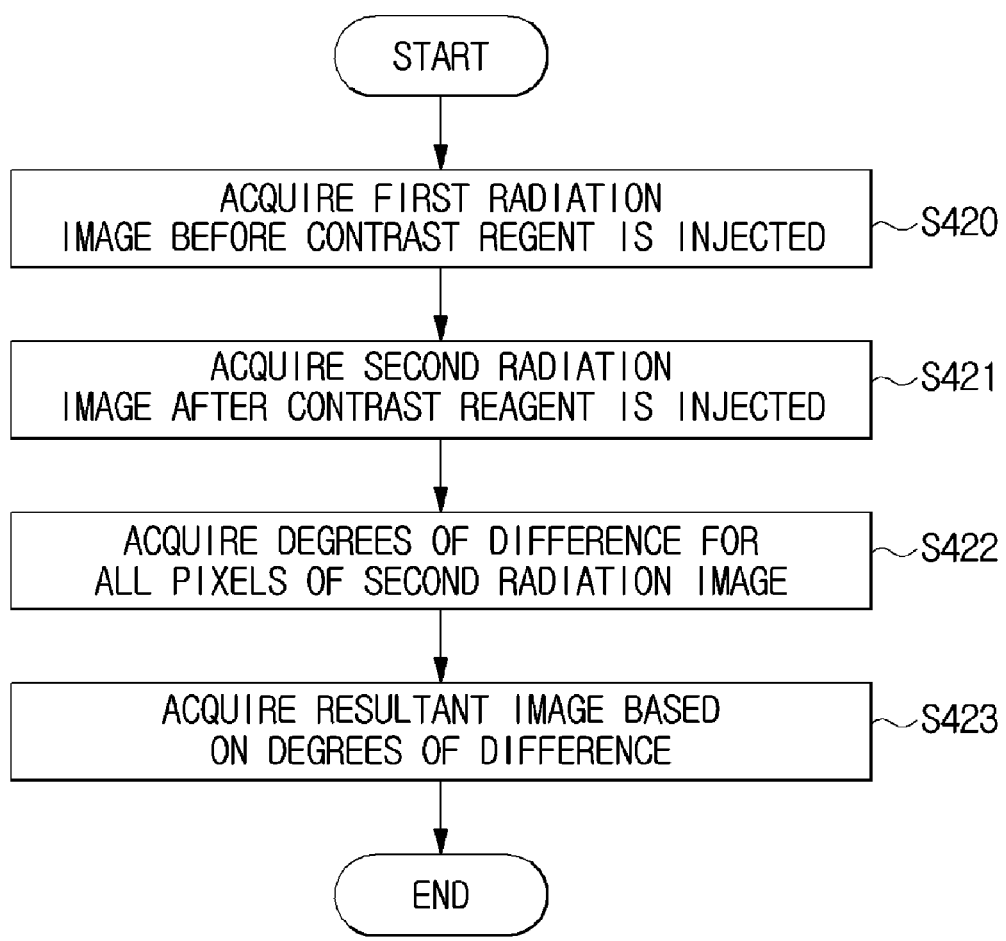
FIG. 22 is a flowchart illustrating a method of controlling a radiography apparatus according to a second exemplary embodiment.

FIG. 22 is a flowchart illustrating a method of controlling a radiography apparatus according to a second exemplary embodiment.

As shown in FIG. 22, in operations S420 and S421, a first radiation image is acquired before a contrast regent is injected into a subject, and a second radiation image is acquired after the contrast reagent is injected into the subject, like the first exemplary embodiment shown in FIG. 21.

In operation S422, the same operations as operations S402 to S410 of the first exemplary embodiment may be performed to acquire degrees of difference for all pixels of the second radiation image.

In operation S423, a resultant image is acquired based on the degrees of difference. In detail, by locating the degrees of difference at locations of the corresponding pixels, an image as shown in FIG. 14 may be acquired. Because a degree of difference for an area through which the contrast reagent passes is different from a degree of difference for an area through which no contrast reagent passes, the image shown in FIG. 14 may also show blood vessels, like a difference image.

Figure 23:
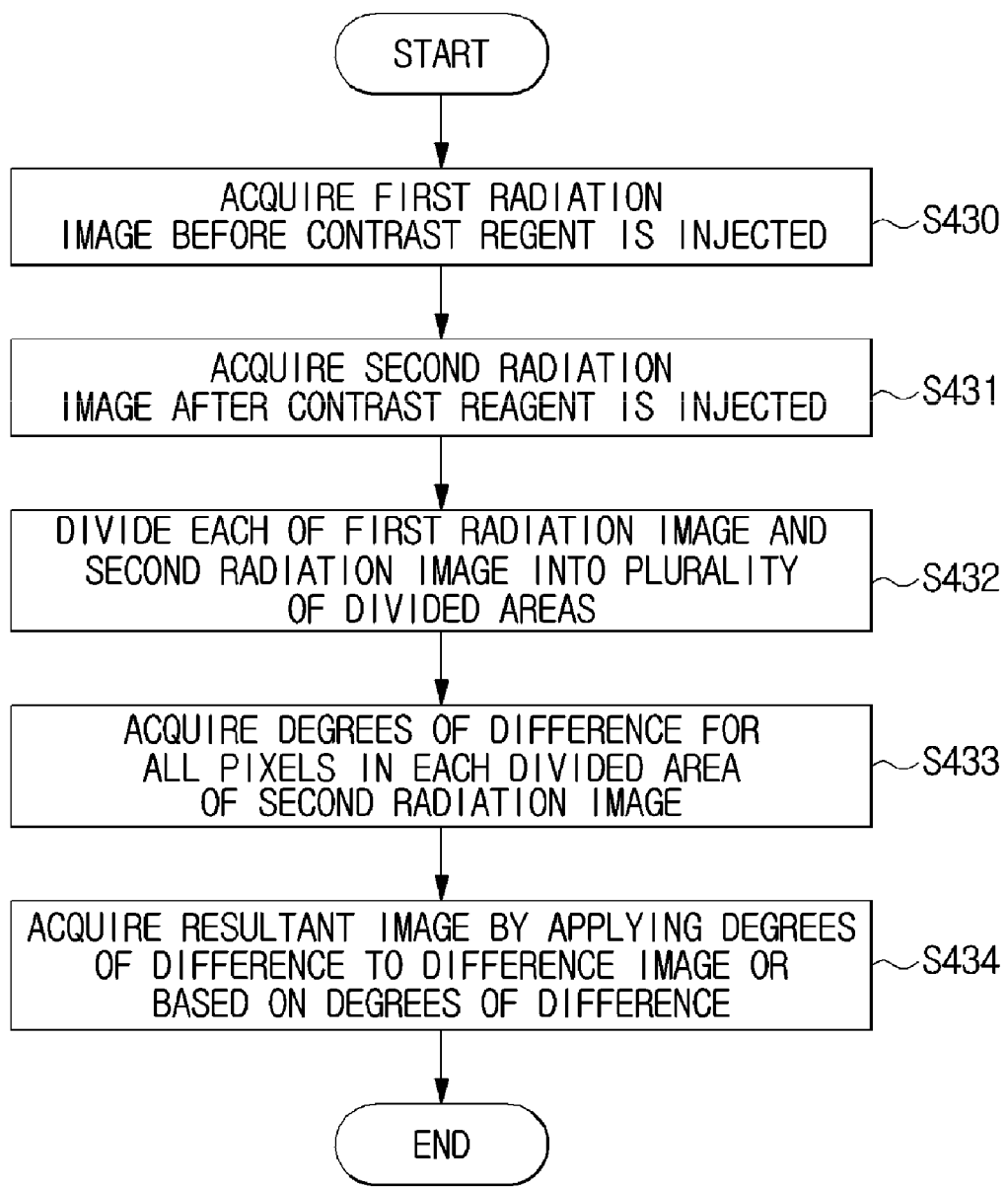
FIG. 23 is a flowchart illustrating a method of controlling a radiography apparatus according to a third exemplary embodiment.

FIG. 23 is a flowchart illustrating a method of controlling a radiography apparatus according to a third exemplary embodiment.

As shown in FIG. 23, in operations S430 and S431, a first radiation image is acquired before a contrast regent is injected into a subject, and a second radiation image is acquired after the contrast reagent is injected into the subject, like the first and second exemplary embodiments shown in FIGS. 21 and 22.

In operation S432, each of the first radiation image and the second radiation image are divided into a plurality of divided areas such that the plurality of divided areas of the first radiation image correspond to the plurality of divided areas of the second radiation image. The plurality of divided areas of the first radiation image may have the same shape or size. According to exemplary embodiments, at least one of the plurality of divided areas may have a shape or size that is different from that of the remaining divided areas. Also, the plurality of divided areas may overlap each other to share a part of pixels of the first radiation image.

Likewise, the plurality of divided areas of the second radiation image may have the same shape or size. Also, according to exemplary embodiments, at least one of the plurality of divided areas may have a shape or size that is different from that of the remaining divided areas. Also, two or more of the plurality of divided areas may overlap a part of the remaining divided areas.

A degree of difference for a pixel in a divided area of the second radiation image is acquired. As described above, the degree of difference for the pixel may be acquired by calculating a difference between a pixel value of the pixel and a pixel value of a pixel in an arbitrary divided area of the first radiation image. By performing the above-described operation on all pixels in the divided area of the second radiation image, degrees of difference for all the pixels of the divided area of the second radiation image are acquired.

In operation S433, by performing the above-described operation on all the divided areas of the second radiation image, degrees of difference for all pixels in each divided area of the second radiation image are acquired.

In operation S434, a resultant image is acquired by applying the degrees of difference to a difference image, or by combining the divided areas based on the degrees of difference.

Figure 24:
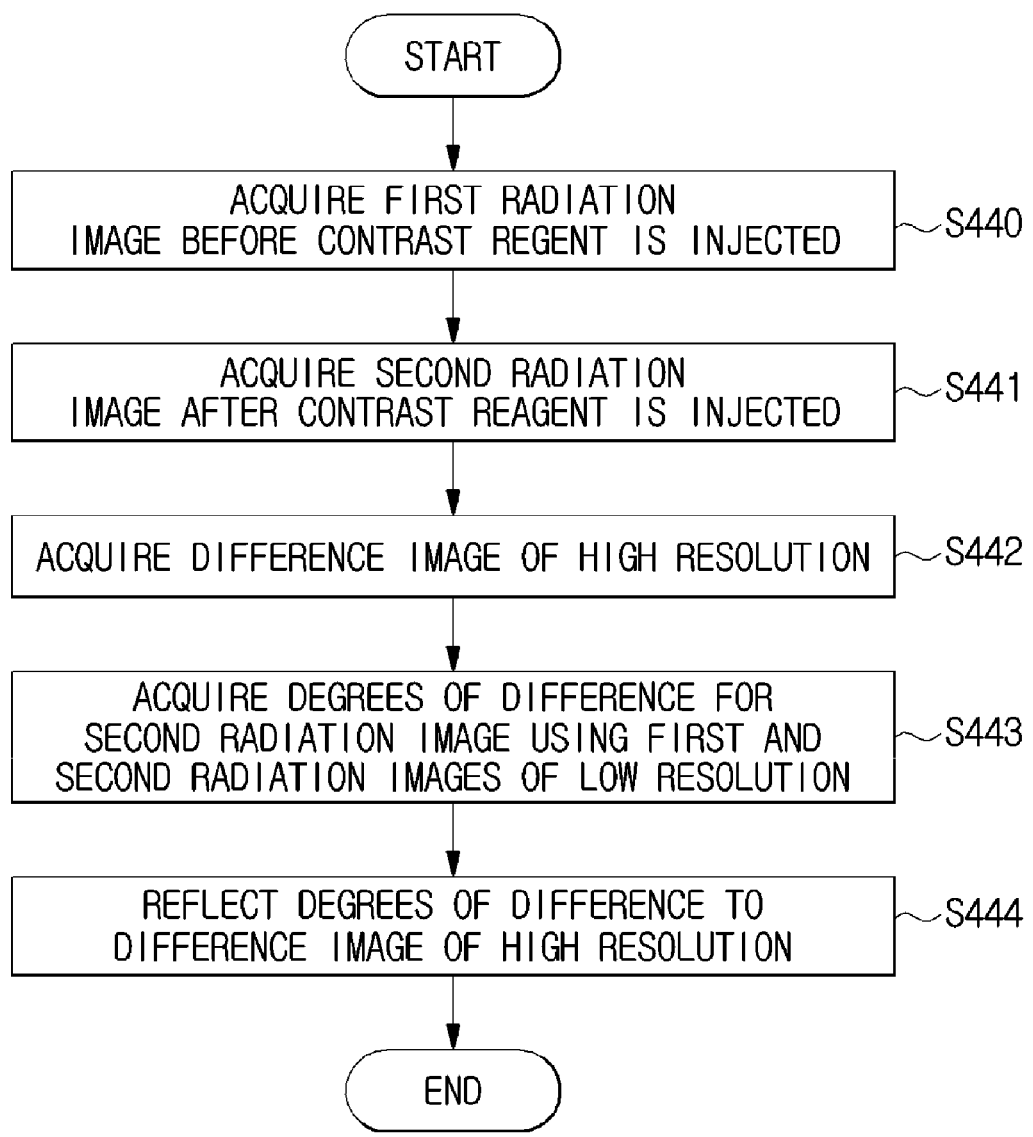
FIG. 24 is a flowchart illustrating a method of controlling a radiography apparatus according to a fourth exemplary embodiment.

FIG. 24 is a flowchart illustrating a method of controlling a radiography apparatus according to a fourth exemplary embodiment.

As shown in FIG. 24, in operations S440 and S441, a first radiation image is acquired before a contrast regent is injected into a subject, and a second radiation image is acquired after the contrast reagent is injected into the subject, like the first, second, and third embodiments shown in FIGS. 21, 22, and 23. In this case, the first radiation image and the second radiation image may be radiation images of relatively high resolutions.

In operation S442, a difference image of a high resolution between the first radiation image and the second radiation image is acquired.

Then, a first radiation image of a relatively low resolution and a second radiation image of a relatively low resolution are acquired from the first radiation image of the relatively high resolution and the second radiation image of the relatively high resolution. The radiation images of the low resolution may be acquired by down-sampling the radiation images of the high resolution.

In operation S443, degrees of difference for all pixels of the second radiation image are acquired using the first radiation image of the relatively low resolution and the second radiation image of the relatively low resolution. Degrees of difference for individual pixels may be acquired by calculating differences between pixel values of all pixels of the first radiation image and a pixel value of an arbitrary pixel of the second radiation image, as described above.

In operation S444, the degrees of difference are reflected to a difference image of a high resolution to acquire a resultant image, or a resultant image of a relatively low resolution formed with the degrees of difference may be up-sampled to acquire a resultant image of a relatively high resolution.

According to the radiography apparatus and the method for controlling the radiography apparatus, it is possible to reduce or remove an artifact on an image, which may be generated upon radiography, thereby acquiring an accurate image about an inside of a subject. It is also possible to reduce or remove an artifact on an image, which may be generated due to movement of a subject during radiography. Further, it is possible to acquire a clear and accurate angiography image about blood vessels in a subject.

In addition, the exemplary embodiments may also be implemented through computer-readable code and/or instructions on a medium, e.g., a non-transitory computer-readable medium, to control at least one processing element to implement any above-described embodiments. The medium may correspond to any medium or media which may serve as a storage and/or perform transmission of the computer-readable code.

The computer-readable code may be recorded and/or transferred on a medium in a variety of ways, and examples of the medium include recording media, such as magnetic storage media (e.g., ROM, floppy disks, hard disks, etc.) and optical recording media (e.g., compact disc read only memories (CD-ROMs) or digital versatile discs (DVDs)), and transmission media such as Internet transmission media. Thus, the medium may have a structure suitable for storing or carrying a signal or information, such as a device carrying a bitstream according to one or more exemplary embodiments. The medium may also be on a distributed network, so that the computer-readable code is stored and/or transferred on the medium and executed in a distributed fashion. Furthermore, the processing element may include a processor or a computer processor, and the processing element may be distributed and/or included in a single device.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of controlling a radiography apparatus, the method comprising:
   acquiring a first radiation image of a subject before a contrast reagent is injected into the subject;
   acquiring a second radiation image of the subject after the contrast reagent is injected into the subject;
   calculating a difference between data of each of a plurality of pixels of the first radiation image and data of one pixel of the second radiation image, respectively; and
   acquiring an image of the subject based on the difference for each of the plurality of pixels of the first radiation image,
   wherein the first radiation image is of a high resolution, and the second radiation image is of the high resolution, and
   the calculating comprises:
      down-sampling the first radiation image of the high resolution and the second radiation image of the high resolution to acquire the first radiation image of a low resolution and the second radiation image of the low resolution; and
      calculating a difference between data of a pixel of the first radiation image of the low resolution and data of a pixel of the second radiation image of the low resolution, for each of pixels of the first radiation image of the low resolution.

2. The method according to claim 1, wherein the calculating comprises calculating a difference between data of a pixel in an area of the first radiation image and data of a pixel in an area of the second radiation image, for each of pixels in the area of the first radiation image.

3. The method according to claim 1, wherein the data of each of the plurality of pixels of the first radiation image and the data of the one pixel of the second radiation image comprise at least one among pixel intensities, values acquired by edge detection, and wavelet coefficients.

4. The method according to claim 1, further comprising:
   dividing the first radiation image into first areas; and
   dividing the second radiation image into second areas.

5. The method according to claim 4, wherein at least two of the first areas of the first radiation image have an overlapping part, or
   at least two of the second areas of the second radiation image have an overlapping part.

6. The method according to claim 4, wherein at least one of the first areas of the first radiation image has a size that is different from a size of one or more remaining ones of the first areas, or
   at least one of the second areas of the second radiation image has a size that is different from a size of one or more remaining ones of the second areas.

7. The method according to claim 1, further comprising:
   subtracting the first radiation image from the second radiation image to acquire a difference image,
   wherein the acquiring comprises correcting the difference image based on the difference for each of the plurality of pixels of the first radiation image, to acquire the image.

8. The method according to claim 1, further comprising:
   determining a degree of difference based on the difference for each of the plurality of pixels of the first radiation image, for each of pixels of the second radiation image,
   wherein the acquiring comprises acquiring the image based on the degree of difference for each of the pixels of the second radiation image.

9. The method according to claim 1, further comprising:
   determining a degree of difference based on the difference for each of the pixels of the first radiation image of the low resolution, for each of pixels of the second radiation image of the low resolution; and
   acquiring an image of the low resolution based on the degree of difference for each of the pixels of the second radiation image of the low resolution,
   wherein the acquiring the image of the subject comprises up-sampling the image of the low resolution to acquire the image of the subject.

10. A radiography apparatus comprising:
    a radiographer configured to:
       acquire a first radiation image of a subject before a contrast reagent is injected into the subject; and
       acquire a second radiation image of the subject after the contrast reagent is injected into the subject; and
    an image processor configured to:
       calculate a difference between data of each of a plurality of pixels of the first radiation image and data of one pixel of the second radiation image, respectively; and
       acquire an image of the subject based the difference for each of the plurality of pixels of the first radiation image,
    wherein the first radiation image is of a high resolution, and the second radiation image is of the high resolution, and
    the image processor is further configured to:
       down-sample the first radiation image of the high resolution and the second radiation image of the high resolution to acquire the first radiation image of a low resolution and the second radiation image of the low resolution; and
       calculate a difference between data of a pixel of the first radiation image of the low resolution and data of a pixel of the second radiation image of the low resolution, for each of pixels of the first radiation image of the low resolution.

11. The radiography apparatus according to claim 10, wherein the image processor is configured to calculate a difference between data of a pixel in an area of the first radiation image and data of a pixel in an area of the second radiation image, for each of pixels in the area of the first radiation image.

12. The radiography apparatus according to claim 10, wherein the data of each of the plurality of pixels of the first radiation image and the data of the one pixel of the second radiation image comprise at least one among pixel intensities, values acquired by edge detection, and wavelet coefficients.

13. The radiography apparatus according to claim 10, wherein the image processor is further configured to:
    divide the first radiation image into first areas; and
    divide the second radiation image into second areas.

14. The radiography apparatus according to claim 13, wherein at least two of the first areas of the first radiation image have an overlapping part, or
    at least two of the second areas of the second radiation image have an overlapping part.

15. The radiography apparatus according to claim 13, wherein at least one of the first areas of the first radiation image has a size that is different from a size of one or more remaining ones of the first areas, or at least one of the second areas of the second radiation image has a size that is different from a size of one or more remaining ones of the second areas.

16. The radiography apparatus according to claim 10, wherein the image processor is further configured to:
   subtract the first radiation image from the second radiation image to acquire a difference image; and
   correct the difference image based on the difference for each of the plurality of pixels of the first radiation image, to acquire the image.

17. The radiography apparatus according to claim 10, wherein the image processor is further configured to:
   determine a degree of difference based on the difference for each of the plurality of pixels of the first radiation image, for each of pixels of the second radiation image; and
   acquire the image based on the degree of difference for each of the pixels of the second radiation image.

18. The radiography apparatus according to claim 10, wherein the image processor is further configured to:
   determine a degree of difference based on the difference for each of the pixels of the first radiation image of the low resolution, for each of pixels of the second radiation image of the low resolution;
   acquire an image of the low resolution based on the degree of difference for each of the pixels of the second radiation image of the low resolution; and
   up-sample the image of the low resolution to acquire the image of the subject.

19. A radiography apparatus comprising:
   an image processor configured to:
      calculate a difference between data of each of a plurality of pixels of a first radiation image of a subject without a contrast reagent and data of one pixel of a second radiation image of the subject with the contrast reagent, respectively;
      determine a degree of difference based on the difference for each of the plurality of pixels of the first radiation image, for each of pixels of the second radiation image; and
      acquire an image of the subject based on the degree of difference for each of the pixels of the second radiation image,
   wherein the first radiation image is of a high resolution, and the second radiation image is of the high resolution, and
   the image processor is further configured to:
      down-sample the first radiation image of the high resolution and the second radiation image of the high resolution to acquire the first radiation image of a low resolution and the second radiation image of the low resolution; and
      calculate a difference between data of a pixel of the first radiation image of the low resolution and data of a pixel of the second radiation image of the low resolution, for each of pixels of the first radiation image of the low resolution.

20. The radiography apparatus according to claim 19, wherein the image processor is further configured to:
   subtract the first radiation image from the second radiation image to acquire a difference image; and
   apply, to the difference image, the degree of difference for each of the pixels of the second radiation image, to acquire the image.

21. The radiography apparatus according to claim 19, wherein the degree of difference is a smallest or greatest value among the difference for each of the plurality of pixels of the first radiation image, or an average value of the difference for each of the plurality of pixels of the first radiation image.

* * * * *